(12) United States Patent
Pezzi

(10) Patent No.: US 10,085,879 B2
(45) Date of Patent: Oct. 2, 2018

(54) HEAT TREATMENT DEVICE

(75) Inventor: Kevin Anthony Pezzi, Thompsonville, MI (US)

(73) Assignee: EMPIRE TECHNOLOGY DEVELOPMENT, LLC, Wilmington, DE (US)

( * ) Notice: Subject to any disclaimer, the term of this patent is extended or adjusted under 35 U.S.C. 154(b) by 0 days.

(21) Appl. No.: 13/637,350

(22) PCT Filed: Apr. 17, 2012

(86) PCT No.: PCT/US2012/033923
§ 371 (c)(1),
(2), (4) Date: Sep. 25, 2012

(87) PCT Pub. No.: WO2013/158076
PCT Pub. Date: Oct. 24, 2013

(65) Prior Publication Data
US 2015/0032192 A1    Jan. 29, 2015

(51) Int. Cl.
*A61F 7/00* (2006.01)
*A61B 90/00* (2016.01)

(52) U.S. Cl.
CPC ........ *A61F 7/007* (2013.01); *A61B 2090/065* (2016.02); *A61F 2007/0054* (2013.01); *A61F 2007/0072* (2013.01); *A61F 2007/0087* (2013.01); *A61F 2007/0096* (2013.01)

(58) Field of Classification Search
CPC ......... A61B 18/04; A61B 18/08; A61B 18/10; A61B 18/12; A61B 18/1266; A61B 18/14; A61B 18/1442; A61B 18/1445; A61B 18/1448; A61B 2019/465; A61F 2007/0054; A61F 2007/0072; A61F 2007/0087; A61F 2007/0096; A61F 2007/007
USPC ................................ 606/33–50; 607/96–104
See application file for complete search history.

(56) References Cited

U.S. PATENT DOCUMENTS

| | | | |
|---|---|---|---|
| 3,847,145 A | 11/1974 | Grossan | |
| 3,848,607 A | 11/1974 | St. Clair | |
| 5,097,828 A | 3/1992 | Deutsch | |
| 5,254,094 A | 10/1993 | Starkey et al. | |
| 5,411,541 A | 5/1995 | Bell et al. | |
| 6,139,570 A * | 10/2000 | Saadat | A61B 18/08 607/105 |
| 6,427,089 B1 * | 7/2002 | Knowlton | A61B 18/18 607/101 |
| 6,623,423 B2 | 9/2003 | Sakurai et al. | |
| 6,907,879 B2 | 6/2005 | Drinan et al. | |

(Continued)

OTHER PUBLICATIONS

"A Device to Enhance TENS Analgesic Effectiveness," Talaria, Inc., accessed at http://www.sbir.gov/sbirsearch/detail/325768, accessed on Apr. 13, 2015, pp. 2.

(Continued)

*Primary Examiner* — Michael Peffley
*Assistant Examiner* — Khadijeh Vahdat

(57) ABSTRACT

A heat treatment device with a handle portion, a tip portion, a power source, and a heating element. The tip portion is heatable to a desired temperature and can be positioned against an affected area for therapeutic treatment. The device can also have control circuitry that can adjust a current flowing to the heating element to regulate the treatment temperature.

14 Claims, 18 Drawing Sheets

(56) References Cited

U.S. PATENT DOCUMENTS

| | | | |
|---|---|---|---|
| 7,211,070 | B2 | 5/2007 | Soroudi |
| 7,314,462 | B2 | 1/2008 | O'Reagan et al. |
| 7,999,412 | B2 | 8/2011 | Lanni |
| 2001/0008974 | A1 | 7/2001 | Li et al. |
| 2002/0068902 | A1 | 6/2002 | Larnard et al. |
| 2003/0159700 | A1* | 8/2003 | Laufer ............ A61B 18/00 128/898 |
| 2003/0233099 | A1 | 12/2003 | Danaek et al. |
| 2004/0120162 | A1 | 6/2004 | Tsimerman |
| 2004/0171970 | A1 | 9/2004 | Schleuniger et al. |
| 2006/0047329 | A1 | 3/2006 | Krespi et al. |
| 2006/0129214 | A1 | 6/2006 | Da Silva et al. |
| 2006/0142824 | A1* | 6/2006 | Zikorus ........... A61B 18/1206 607/96 |
| 2007/0016254 | A1 | 1/2007 | Grenon |
| 2007/0106247 | A1 | 5/2007 | Burnett et al. |
| 2007/0129711 | A1 | 6/2007 | Altshuler et al. |
| 2007/0255356 | A1 | 11/2007 | Rose et al. |
| 2008/0015540 | A1 | 1/2008 | Muni et al. |
| 2008/0046048 | A1 | 2/2008 | Grenon et al. |
| 2008/0097295 | A1 | 4/2008 | Makower et al. |
| 2008/0139974 | A1 | 6/2008 | Da Silva |
| 2008/0195230 | A1* | 8/2008 | Quijano .......... A61B 17/3203 623/23.72 |
| 2008/0319372 | A1 | 12/2008 | Palti et al. |
| 2009/0113618 | A1 | 5/2009 | Slayton |
| 2009/0281454 | A1 | 11/2009 | Baker et al. |
| 2010/0016852 | A1* | 1/2010 | Manzo ............ A61B 18/1445 606/46 |
| 2010/0125255 | A1 | 5/2010 | Paulson |
| 2010/0179623 | A1 | 7/2010 | Hofer et al. |
| 2010/0185192 | A1 | 7/2010 | Muller et al. |
| 2012/0078166 | A1 | 3/2012 | Hoke et al. |
| 2012/0116217 | A1 | 5/2012 | Lee-Sepsick et al. |
| 2012/0165668 | A1 | 6/2012 | Slayton et al. |
| 2012/0209177 | A1 | 8/2012 | Boghossian |
| 2013/0041292 | A1* | 2/2013 | Cunningham ....... A61B 18/12 601/2 |
| 2014/0200507 | A1 | 7/2014 | Azeez |

OTHER PUBLICATIONS

"Abscess," accessed at https://web.archive.org/web/20120223071101/http://en.wikipedia.org/wiki/Abscess, last modified on Jan. 23, 2012, pp. 6.
"Adverse drug reaction," accessed at https://web.archive.org/web/20120301153220/http://en.wikipedia.org/wiki/Adverse_drug_reaction, last modified on Feb. 5, 2012, pp. 7.
"Aerogel," accessed at https://web.archive.org/web/20120406155356/http://en.wikipedia.org/wiki/Aerogel, last modified on Mar. 27, 2012, pp. 9.
"Allotropy," accessed at https://web.archive.org/web/20120310174841/http://en.wikipedia.org/wiki/Allotrope, last modified on Mar. 8, 2012, pp. 7.
"Alopecia," accessed at https://web.archive.org/web/20120305122043/http://en.wikipedia.org/wiki/Hair_loss, last modified on Feb. 28, 2012, pp. 5.
"Auricle (anatomy)," accessed at https://web.archive.org/web/20150319205059/https://en.wikipedia.org/wiki/Auricle_(anatomy), last modified on Feb. 2, 2015, pp. 7.
"Blue Light Destroys Antibiotic-Resistant Staph Infection," Science Daily, accessed at https://web.archive.org/web/20111228072117/http://www.sciencedaily.com/releases/2009/01/090129131839.htm, posted on Jan. 29, 2009, pp. 2.
"Boil," accessed at https://web.archive.org/web/20120124162330/http://en.wikipedia.org/wiki/Boil, last modified on Jan. 24, 2012, pp. 5.
"Bursitis," accessed at https://web.archive.org/web/20120223184141/http://en.wikipedia.org/wiki/Bursitis, last modified on Feb. 18, 2012, pp. 4.

"Carboxymethyl cellulose," accessed at https://web.archive.org/web/20111121115646/http://en.wikipedia.org/wiki/Carboxymethyl_cellulose, last modified on Oct. 26, 2011, pp. 3.
"Carbuncle," accessed at https://web.archive.org/web/20120324131903/http://en.wikipedia.org/wiki/Carbuncle, last modified on Feb. 9, 2012, pp. 4.
"Cellulitis," accessed at https://web.archive.org/web/20120126132357/http://en.wikipedia.org/wiki/Cellulitis, last modified on Dec. 1, 2011, pp. 6.
"Color Sensor : TCS3103FN," accessed at https://web.archive.org/web/20111215202929/http://www.taosinc.com/ProductDetails.aspx?id=131, accessed on Apr. 13, 2015, pp. 1.
"Common bile duct," accessed at https://web.archive.org/web/20120204214416/http://en.wikipedia.org/wiki/Common_bile_duct, last modified on May 6, 2011, pp. 6.
"CoolPoly® D8102 Thermally Conductive Thermoplastic Elastomer (TPE)," Cool Polymers, Preliminary Product Data, accessed at https://web.archive.org/web/20120105131906/http://www.coolpolymers.com/Files/DS/Datasheet_d8102.pdf, posted on Jun. 30, 2009, pp. 1.
"Cracked Fingertips Add to Winter's Misery," accessed at https://web.archive.org/web/20120415123430/http://www.peoplespharmacy.com/2007/12/17/cracked-fingert/, posted on Dec. 17, 2007, pp. 26.
"Curing and Smoking Meats for Home Food Preservation Literature Review and Critical Preservation Points," accessed at https://web.archive.org/web/20120323070326/http://nchfp.uga.edu/publications/nchfp/lit_rev/cure_smoke_fs.html, accessed on Apr. 13, 2015, pp. 6.
"Dandruff," accessed at https://web.archive.org/web/20120301050038/https://en.wikipedia.org/wiki/Dandruff, last modified on Feb. 20, 2012, pp. 6.
"Diabetic foot ulcer," accessed at https://web.archive.org/web/20120224194406/https://en.wikipedia.org/wiki/Diabetic_foot_ulcer, last modified on Feb. 3, 2012, pp. 9.
"Dielectric heating," accessed at https://web.archive.org/web/20120224175014/http://en.wikipedia.org/wiki/Dielectric_heating, last modified on Feb. 22, 2012, pp. 5.
"Emissivity," accessed at https://web.archive.org/web/20120121060208/http://en.wikipedia.org/wiki/Emissivity, last modified on Dec. 20, 2011, pp. 4.
"Endoscopic Retrograde Cholangiopancreatogram (ERCP)," Digestive Disorders Health Center, accessed at https://web.archive.org/web/20120401000705/http://www.webmd.com/digestive-disorders/endoscopic-retrograde-cholangiopancreatogram-ercp?, last Updated on Apr. 8, 2011, pp. 2.
"Epigenetics," accessed at https://web.archive.org/web/20120128203741/http://en.wikipedia.org/wiki/Epigenetics, last modified on Jan. 17, 2012, pp. 13.
"Erysipelas," accessed at https://web.archive.org/web/20120404183347/https://en.wikipedia.org/wiki/Erysipelas, last modified on Apr. 3, 2012, pp. 6.
"Eye Health Center," accessed at https://web.archive.org/web/20120411212258/http://www.webmd.com/eye-health/tc/styes-and-chalazia-topic-overview, accessed at last updated on Apr. 14, 2011, pp. 2.
"Folliculitis Symptoms—Diseases and Conditions—Mayo Clinic," accessed at https://web.archive.org/web/20140122003902/http://www.mayoclinic.org/diseases-conditions/folliculitis/basics/symptoms/con-20025909, accessed on Apr. 13, 2015, pp. 4.
"Gain scheduling," accessed at https://web.archive.org/web/20120126001711/http://en.wikipedia.org/wiki/Gain_scheduling, last modified on Dec. 3, 2011, pp. 2.
"Gingivitis," Pubmed Health, accessed at http://www.ncbi.nlm.nih.gov/pubmedhealth/PMHT0023280/, accessed on Apr. 13, 2015, pp. 1.
"Globe (human eye)," accessed at https://web.archive.org/web/20120113193707/http://en.wikipedia.org/wiki/Globe_(human_eye), last modified on Nov. 5, 2011, pp. 3.
"Graphane," accessed at https://web.archive.org/web/20101126205822/http://en.wikipedia.org/wiki/Graphane, last modified on Nov. 19, 2010, pp. 1.
"Graphene," accessed at https://web.archive.org/web/20120126004904/http://en.wikipedia.org/wiki/Graphene, last modified on Jan. 25, 2012, pp. 25.

(56) References Cited

OTHER PUBLICATIONS

"Guar gum," accessed at https://web.archive.org/web/20120223233128/https://en.wikipedia.orgiwiki/Guar_gum, last modified on Feb. 16, 2012, pp. 6.
"Halide," accessed at https://web.archive.org/web/20120306060018/http://en.wikipedia.org/wiki/Halide, last modified on Feb. 21, 2012, pp. 4.
"Healthcare-associated Infections (HAI)," Centre for Disease Control and Prevention, accessed at https://web.archive.org/web/20120415221654/http://www.cdc.gov/hai/, last updated on Nov. 2, 2011, pp. 2.
"Heat capacity," accessed at https://web.archive.org/web/20120131034722/http://en.wikipedia.org/wiki/Heat_capacity, last modified on Jan. 30, 2012, pp. 19.
"Highlights of Prescribing Information," Latisse, Allergan, Inc. pp. 12 (2014).
"Hordeolum (Stye)," The Ohio State University Medical Centre, accessed at https://web.archive.org/web/20110918003135/http://medicalcenter.osu.edu/patientcare/healthcare_services/pediatrics/common_childhood_illness/eye_conditions/hordeolum_stye/Pages/index.aspx, accessed on Apr. 13, 2015, pp. 2.
"How widespread is the problem of hospital-acquired infections (HAIs)?," NCSL, accessed at http://web.archive.org/web/20101122202514/http://www.ncsl.org/?TabId=13970, accessed on Apr. 14, 2015, pp. 2.
"Hydroxypropyl cellulose," accessed at https://web.archive.org/web/20120113060722/http://en.wikipedia.org/wiki/Hydroxypropyl_cellulose, last modified on Dec. 30, 2011, pp. 3.
"Impetigo," accessed at https://web.archive.org/web/20120119090953/http://en.wikipedia.org/wiki/Impetigo, last modified on Dec. 26, 2011, pp. 5.
"Infecting Hospital Staff With Contagious Awareness," Science Daily, accessed at https://web.archive.org/web/20120120164216/http://www.sciencedaily.com/releases/2011/10/111014122533.htm, posted on Oct. 14, 2011, pp. 2.
"Infrared Thermometer," accessed at https://web.archive.org/web/20120226010147/http://www.omega.com/prodinfo/infraredthermometerh.tml, accessed on Apr. 13, 2015, pp. 4.
"Latisse," accessed at http://web.archive.org/web/20120113171243/http://www.latisse.com/?cid=ppc_gg_latisse, accessed on Apr. 14, 2015, pp. 2.
"Methicillin-resistant *Staphylococcus aureus*," accessed at https://web.archive.org/web/20120413061701/http://en.wikipedia.org/wiki/Methicillin-resistant_Staphylococcus_aureus, last modified on Apr. 12, 2012, pp. 20.
"Methyl cellulose," accessed at https://web.archive.org/web/20111118010456/http://en.wikipedia.org/wiki/Methyl_cellulose, last modified on Nov. 12, 2011, pp. 6.
"Microwaves to fight infection," Swinburne University of Technology: Applied and Environmental Microbiology, accessed at http://www.myvmc.com/news/microwaves-to-fight-infection/, modified on Jan. 15, 2014, pp. 6.
"Minimum bactericidal concentration," accessed at https://web.archive.org/web/20110418200046/http://en.wikipedia.org/wiki/Minimum_Bactericidal_Concentration, Oct. 17, 2010, pp. 1.
"Minimum inhibitory concentration," accessed at https://web.archive.org/web/20111116183825/http://en.wikipedia.org/wiki/Minimum_inhibitory_concentration, last modified on Sep. 26, 2011, pp. 3.
"Necrotizing fasciitis," accessed at https://web.archive.org/web/20120227030441/https://en.wikipedia.org/wiki/Necrotizing_fasciitis, last modified on Feb. 26, 2012, pp. 7.
"New Research Estimates MRSA Infections Cost U.S. Hospitals $3.2 Billion to $4.2 Billion Annually," accessed at https://web.archive.org/web/20110606002337/http://www.infectioncontroltoday.com/news/2005/05/new-research-estimates-mrsa-infections-cost-u-s-h.aspx, posted on May 16, 2005, pp. 1.
"Nitric oxide synthase," accessed at https://web.archive.org/web/20150409054640/http://en.wikipedia.org/wiki/Nitric_oxide_synthase, last modified on Apr. 7, 2015, pp. 8.

"Ofloxacin Ophthalmic," AHFS Consumer Medication Information, accessed at https://web.archive.org/web/20120829050252/http://www.ncbi.nlm.nih.gov/pubmedhealth/PMH0000208/, last revision on Jan. 1, 2011, pp. 3.
"Periodontal disease," University of Maryland Medical Centre, accessed at https://web.archive.org/web/20130625234625/http://umm.edu/health/medical/reports/articles/periodontal-disease, last updated on Jun. 24, 2013, pp. 12.
"Periodontitis," NIH—National Institute of Arthritis and Musculoskeletal and Skin Diseases, accessed at http://www.ncbi.nlm.nih.gov/pubmedhealth/PMHT0023281/, accessed on Apr. 14, 2015, pp. 2.
"PID controller," accessed at https://web.archive.org/web/20120120190916/http://en.wikipedia.org/wiki/PID_controller, last modified on Jan. 13, 2012, pp. 18.
"Plasma Therapy: An Alternative to Antibiotics?," accessed at https://web.archive.org/web/20120411031104/http://www.sciencedaily.com/releases/2010/12/101215092248.htm, posted on Dec. 15, 2010, pp. 2.
"Rifling," accessed at https://web.archive.org/web/20120110102647/http://en.wikipedia.org/wiki/Rifling, last modified on Dec. 14, 2011, pp. 10.
"Septic Bursitis," Family Practice Note Book, accessed at http://web.archive.org/web/20111226194821/http://www.fpnotebook.com/Ortho/ID/SptcBrsts.htm, accessed on Apr. 14, 2015, pages.
"Silicone Rubber Heaters," accessed at https://web.archive.org/web/20120225164709/http://www.hiheat.com/products/silicone-rubber-heaters, accessed on Apr. 13, 2015, pp. 3.
"Standard of care," accessed at https://web.archive.org/web/20120224023956/https://en.wikipedia.org/wiki/Standard_of_care, last modified on Dec. 7, 2011, pp. 5.
"*Staphylococcus aureus*," accessed at https://web.archive.org/web/20120224195752/https://en.wikipedia.org/wiki/Staphylococcus_aureus, last modified on Feb. 15, 2012, pp. 12.
"Tendinitis," accessed at https://web.archive.org/web/20120212094717/http://en.wikipedia.org/wiki/Tendinitis, last modified on Jan. 14, 2012, pp. 4.
"Tendinosis," accessed at https://web.archive.org/web/20120209231527/http://en.wikipedia.org/wiki/Tendinosis, last modified on Dec. 2, 2011, pp. 6.
"Tennis elbow," accessed at https://web.archive.org/web/20120301182617/http://en.wikipedia.org/wiki/Tennis_elbow, last modified on Feb. 20, 2012, pp. 8.
"The Bacteriology of the *Staphylococci*," accessed at https://web.archive.org/web/20120324051625/http://cmgm.stanford.edu/micro/MI209/Staphylococcus%20aureus.pdf, accessed on Apr. 13, 2015, pp. 55.
"Use of Pulsed Electric Fields and Electrolyzed Oxidizing Water to Control Listeria," accessed at https://web.archive.org/web/20110820224059/http://www.amif.org/ht/a/GetDocumentAction/i/7422, posted on Oct. 1999, pp. 2.
"Venous ulcer," accessed at https://web.archive.org/web/20120104090509/http://en.wikipedia.org/wiki/Venous_ulcer, last modified on Nov. 10, 2011, pp. 5.
"Wood's metal," accessed at https://web.archive.org/web/20120401080025/http://en.wikipedia.org/wiki/Wood%27s_metal, last modified on Feb. 19, 2012, pp. 4.
Adler, J., and Shi, W., "Galvanotaxis in Bacteria," Cold Spring Harbor Symposia on Quantitative Biology, vol. 53, pp. 23-25 (1988).
Akiyama, H., et al., "Changes in *Staphylococcus aureus* density and lesion severity after topical application of povidone-iodine in cases of atopic dermatitis," Journal of Dermatological Science, vol. 16, Issue 1, pp. 23-30 (Nov. 1997).
Amiali, M., et al., "Synergistic effect of temperature and pulsed electric field on inactivation of *Escherichia coli* O157: H7 and *Salmonella enteritidis* in liquid egg yolk," Journal of Food Engineering, vol. 79, Issue 2, pp. 689-694 (2007).
Anderson, D. J., et al., "Clinical and Financial Outcomes Due to Methicillin Resistant *Staphylococcus aureus* 23 Surgical Site Infection: A Multi-Center Matched Outcomes Study," PLoS One, vol. 4, Issue 12, pp. 1-8 (Dec. 2009).

(56) References Cited

OTHER PUBLICATIONS

Ark, P. A., "Application of High-Frequency Electrostatic Fields in Agriculture," The Quarterly Review of Biology, vol. 15, No. 2, pp. 172-191 (Jun. 1940).

Aronsson, K., et al., "Inactivation of microorganisms using pulsed electric fields: the influence of process parameters on *Escherichia coli, Listeria innocua, Leuconostoc mesenteroides* and *Saccharomyces cerevisiae*," Innovative Food Science & Emerging Technologies, vol. 2, Issue 1, pp. 41-54 (Mar. 2001).

Arshad, M., et al., "Sensitivity and spectrum of bacterial isolates in infectious otitis externa," Journal of the College of Physicians and Surgeons Pakistan, vol. 14, Issue 3, pp. 146-149 (Mar. 2004).

Bergen, C. J. V., et al., "Pulsed electromagnetic fields after arthroscopic treatment for osteochondral defects of the talus: double-blind randomized controlled multicenter trial," BMC Musculoskeletal Disorders, vol. 10, pp. 1-10 (Jul. 10, 2009).

Bertin, M.L., et al., "Outbreak of methicillin-resistant *Staphylococcus aureus* colonization and infection in a neonatal intensive care unit epidemiologically linked to a healthcare worker with chronic otitis," Infection Control and Hospital Epidemiology, vol. 27, No. 6, pp. 581-585 (Jun. 2006).

Beveridge, J. R., et al., "Pulsed electric field inactivation of spoilage microorganisms in alcoholic beverages," Proceedings of the IEEE, vol. 92, Issue 7, pp. 1138-1143 (Jul. 2004).

Boguniewicz, M., and Leung, DY., "Recent insights into atopic dermatitis and implications for management of infectious complications," J Allergy Clin Immunol., vol. 125, Issue 1, pp. 4-13 (Jan. 2010).

Boopalan, PR., et al., "Pulsed electromagnetic field therapy results in healing of full thickness articular cartilage defect," International Orthopaedics (SICOT), vol. 35, Issue 1, pp. 143-148 (Jan. 2011).

Boyle, R., et al., "A Blast of Cold Plasma Kills Drug-Resistant Bacteria," accessed at https://web.archive.org/web/20101219115113/http://www.popsci.com/science/article/2010-12/cold-plasma-treatment-kills-drug-resistant-bacteria-heralding-new-antibiotic-alternative, posted on Dec. 15, 2010, pp. 2.

Breuer, K., et al., "*Staphylococcus aureus*: colonizing features and influence of an antibacterial treatment in adults with atopic dermatitis," British Journal of Dermatology, vol. 147, Issue 1, pp. 55-61 (Jul. 2002).

Brook, I., "Bacterial flora of airline headset devices," American Journal of Otolaryngology, vol. 6, No. 2, pp. 111-114 (Mar.-Apr. 1985).

Brook, I., "Bacterial Flora of Stethoscopes' Earpieces and Otitis Externa," The Annals of otology, rhinology, and laryngology, vol. 106, No. 9, pp. 751-752 (Sep. 1997).

Brook, I., "Secondary bacterial infections complicating skin lesions," Journal of Medical Microbiology, vol. 55, No. 10, pp. 808-812 (Oct. 2002).

Brusch, J. L., et al., "Septic Arthritis," accessed at http://emedicine.medscape.com/article/236299-overview, updated on Mar. 28, 2014, pp. 3.

Callaghan, MJ, et al., "Pulsed electromagnetic fields accelerate normal and diabetic wound healing by increasing endogenous FGF-2 release," Plastic & Reconstructive Surgery, vol. 121, Issue 1, pp. 130-141 (Jan. 2008).

Cantrell, H.F. et al. Declining susceptibility to neomycin and polymyxin B of pathogens recovered in otitis externa clinical trials, Southern Medical Journal, vol. 97, Issue 5, pp. 465-471 (May 1, 2004).

Case, C. L., "Handwashing," Access Excellence Classic Collection, accessed at https://web.archive.org/web/20120402193942/http://www.accessexcellence.org/AE/AEC/CC/hand_background.php, accessed on Apr. 14, 2015, pp. 4.

Costerton, J. W., et al., "Mechanism of electrical enhancement of efficacy of antibiotics in killing biofilm bacteria," Antimicrobial Agents and Chemotherapy, vol. 38, No. 12, pp. 2803-2809 (Dec. 1994).

Dallari, D., et al., "Effects of pulsed electromagnetic stimulation on patients undergoing hip revision prostheses: A randomized prospective double-blind study," Bioelectromagnetics, vol. 30, Issue 6, pp. 423-430 (Sep. 2009).

Dibb, WL., "Microbial aetiology of otitis externa," Journal of Infection, vol. 22, Issue 3, pp. 233-239 (May 1991).

Dike, O. U., and Geveke, D. J., "A combined treatment of UV-light and radio frequency electric field for the inactivation of *Escherichia coli* K-12 in apple juice," International Journal of Food Microbiology, vol. 138, Issues 1-2, pp. 50-55 (Mar. 31, 2010).

Dimond, A., and Duggar, B. M., "Some Lethal Effects of Ultra-Violet Radiation of Fungus Spores," Proc Natl Acad Sci U S A., vol. 27, No. 10, pp. 459-468 (Oct. 15, 1951).

Draper, D. O., et al., "Hot-Pack and 1-MHz Ultrasound Treatments Have an Additive Effect on Muscle Temperature Increase," Journal of Athletic Training, vol. 33, No. 1, pp. 21-24 (Jan.-Mar. 1998).

Drees, K. P., et al., "Comparative electrochemical inactivation of bacteria and bacteriophage," Water Research, vol. 37, pp. 2291-2300 (May 2003).

Dusto, A., "Cold Plasma Kills Bacteria Better Than Antibiotics," Biotechnology, accessed at https://web.archive.org/web/20130320041148/http://news.discovery.com/tech/biotechnology/cold-plasma-kills-bacteria-better-than-antibiotics.htm, posted on Dec. 18, 2010, pp. 4.

Ermolaeva, S. A., et al., "Bactericidal effects of non-thermal argon plasma in vitro, in biofilms and in the animal model of infected wounds," Journal of Medical Microbiology, vol. 60, No. 1, pp. 75-83 (Jan. 2011).

Falagas, M. e., et al., "Comparison of antibiotics with placebo for treatment of acute sinusitis: a meta-analysis of randomised controlled trials," The Lancet Infectious Diseases, vol. 8, No. 9, pp. 543-552 (Sep. 2008).

Fernández-Molina, J. J., et al., "The Combined Effect of Pulsed Electric Fields and Conventional Heating on the Microbial Quality and Shelf Life of Skim Milk," Journal of Food Processing and Preservation, vol. 29, Issue 5-6, pp. 390-406 (Oct. 2005).

Fini, M., et al., "Effect of pulsed electromagnetic field stimulation on knee cartilage, subchondral and epyphiseal trabecular bone of aged Dunkin Hartley guinea pigs," Biomedicine & Pharmacotherapy, vol. 62, Issue 10, pp. 709-715 (Dec. 2008).

Fletcher, LA, et al., "Bactericidal action of positive and negative ions in air," BMC Microbiology, vol. 7, Issue 32, pp. 1-9 (Apr. 17, 2007).

Foley, KT, et al., "Randomized, prospective, and controlled clinical trial of pulsed electromagnetic field stimulation for cervical fusion," The Spine Journal, vol. 8, Issue 3, pp. 436-442 (May-Jun. 2008).

Galvagno, M. A., et al., "Exploring the use of natural antimicrobial agents and pulsed electric fields to control spoilage bacteria during a beer production process," Revista Argentina de Microbiologia, vol. 39, Issue 3, pp. 170-176 (Jul.-Sep. 2007).

Ganesan, K., et al., "Low frequency pulsed electromagnetic field—a viable alternative therapy for arthritis," Indian Journal of Experimental Biology, vol. 47, pp. 939-948 (Dec. 2009).

Geveke, D. J. and Brunkhorst, C., "Inactivation of *Saccharomyces cerevisiae* with Radio Frequency Electric Fields," Journal of Food Protection, vol. 66, No. 9, pp. 1712-1715 (Sep. 2003).

Giladi, M., et al., "Microbial growth inhibition by alternating electric fields," Antimicrobial Agents and Chemotherapy, vol. 52, Issue 10, pp. 3517-3522 (Oct. 2008).

Gómez-Ochoa, I., et al., "Pulsed electromagnetic fields decrease proinflammatory cytokine secretion (IL-1β and TNF-α) on human fibroblast-like cell culture," Rheumatology International, vol. 31, Issue 10, pp. 1283-1289 (Oct. 2011).

Goudarzi, I., et al., "Pulsed electromagnetic fields accelerate wound healing in the skin of diabetic rats," Bioelectromagnetics, vol. 31, Issue 4, pp. 318-323 (May 2010).

Graak, V. et al., "Evaluation of the efficacy of pulsed electromagnetic field in the management of patients with diabetic polyneuropathy," Int J Diabetes Dev Ctries, vol. 29, Issue 2, pp. 56-61 (Apr.-Jun. 2009).

Grahl, T., and Markl, H., "Killing of microorganisms by pulsed electric fields," Applied Microbiology and Biotechnology, vol. 45, Issue 1-2, pp. 148-157 (Mar. 1996).

(56) References Cited

OTHER PUBLICATIONS

Gross, B., et al., "An examination of the effect of an AC pulsed electric field on cell mortality in SWLA-2 hybridomas," 26th Annual International Conference of the IEEE Engineering in Medicine and Biology Society, IEMBS '04, vol. 1, pp. 2635-2638 (Sep. 1-5, 2004).
Gupta, AK., et al., "Pulsed electromagnetic stimulation in nonunion of tibial diaphyseal fractures," Indian Journal of Orthopaedics, vol. 43, Issue 2, pp. 156-160 (Apr. 2009).
Handzel, O., and Halperin, D., et al., "Necrotizing (Malignant) External Otitis," American Family Physician, vol. 68, No. 2, pp. 309-312 (Jul. 15, 2003).
Harris, D., "Diseases Caused by *Staphylococcus Aureus*," accessed at https://web.archive.org/web/20100618060756/http://www.ehow.com/how-does_5480244_diseases-caused-staphylococcus-aureus.html, accessed on Apr. 13, 2015, pp. 2.
Hata, T. R., et al., "Antimicrobial Peptides, Skin Infections and Atopic Dermatitis," Semin Cutan Med Surg., vol. 27, Issue 2, pp. 144-150 (Jun. 2008).
Hernando-Harder, A. C., et al., "Helicobacter pylori infection and dermatologic diseases," European Journal of Dermatology, vol. 19, No. 5, pp. 431-444 (Sep.-Oct. 2009).
Hülsheger, H., et al., "Electric field effects on bacteria and yeast cells," Radiation and Environmental Biophysics, vol. 22, Issue 2, pp. 149-162 (1983).
Hülsheger, H., et al "Killing of bacteria with electric pulses of high field strength," Radiation and Environmental Biophysics, vol. 20, Issue 1, pp. 53-65 (1981).
Hwang, JH., et al., "Community-acquired methicillin-resistant *Staphylococcus aureus* infections in discharging ears," Acta Otolaryngologica, vol. 122, Issue 8, pp. 827-830 (Dec. 2002).
Inhan-Garip, A., et al., "Effect of extremely low frequency electromagnetic fields on growth rate and morphology of bacteria," International Journal of Radiation Biology, vol. 87, No. 12, pp. 1155-1161 (Dec. 2011).
Kandlikar, S., et al., "An examination of the effect of decaying exponential pulse electric fields on cell mortality in murine spleenocytes, hybridomas, and human natural killer cells," Conf Proc IEEE Eng Med Biol Soc., vol. 4, pp. 2643-2646 (2004).
Keles, C., et al., "Inactivation of *Salmonella* spp. by Low-Frequency Electric Fields in Sewage Sludge," International Journal of Civil & Environmental Engineering, vol. 10 No. 6, pp. 13-18 (Dec. 2010).
King, R. W., et al., "Staphylococcal Scalded Skin Syndrome," accessed at http://emedicine.medscape.com/article/788199-overview, updated on Feb. 6, 2014, pp. 3.
Kirawanich, P., et al., "Microorganism Inactivation by Nanosecond Pulsed Electric Fields: Full-wave Analysis and Experiment," International Conference on Food Engineering and Biotechnology, IPCBEE, vol. 9, pp. 6-11 (2011).
Kirman, C. N., et al., "Pressure Ulcers and Wound Care," accessed at http://emedicine.medscape.com/article/190115-overview, updated on Apr. 1, 2015, pp. 9.
Kluytmans, J., et al., "Nasal Carriage of *Staphylococcus aureus*: Epidemiology, Underlying Mechanisms, and Associated Risks," Clinical Microbiology Reviews, vol. 10, No. 3, pp. 505-520 (Jul. 1997).
Kumar, A., et al., "Electric field induced bacterial flocculation of enteroaggregative *Escherichia coli* 042," Applied Physics Letters, vol. 98, Issue 25, pp. 253701-253701-3 (Jun. 2011).
Lamba, B., "Advent of Cold Plasma," accessed at https://web.archive.org/web/20121028010048/http://m.phys.org/_news6688.html, posted on Sep. 22, 2005, pp. 1.
Leary, R. O., et al., "The bactericidal effects of dental ultrasound on Actinobacillus actinomycetemcomitans and Porphyromonas gingivalis. An in vitro investigation," Journal of Clinical Periodontology, vol. 24, Issue 6, pp. 432-439 (Jun. 1997).
Leung, D. Y., "Infection in atopic dermatitis," Current Opinion in Pediatrics, vol. 15, Issue 4, pp. 399-404 (Aug. 2003).

Liakos, T., et al., "Methicillin-resistant *Staphylococcus aureus* laryngitis," The Annals of otology, rhinology, and laryngology, vol. 119, Issue 9, pp. 590-593 (Sep. 2010).
Lilenbaum, W., et al., "Antimicrobial susceptibility of staphylococci isolated from otitis externa in dogs," Letters in Applied Microbiology, vol. 31, Issue 1, pp. 42-45 (Jul. 2000).
Lübbe, J., "Secondary Infections in Patients with Atopic Dermatitis," American Journal of Clinical Dermatology, vol. 4, Issue 9, pp. 641-654 (Sep. 2003).
Lv, I., et al., "[Low-frequency magnetic field in the combined therapy of inflammatory lung diseases]," Prob Tuberk, vol. 3, pp. 53-56 (1988).
Machekhin, VA, et al., "[a new method for treating chronic blepharitis using magnetic compounds and an alternating magnetic field]," Vestn Oftalmol., vol. 109, Issue 4, pp. 16-18 (Jul.-Sep. 1993).
Malicki, A., et al., "Effect of Pulsed Electric Field (PEF) on *Escherichia coli* Within the Liquid Whole Egg," Bull Vet Inst Pulawy, vol. 48, pp. 371-374 (2004).
Matic, M., et al., "Influence of different types of electromagnetic fields on skin reparatory processes in experimental animals," Lasers in Medical Science, vol. 24, Issue 3, pp. 321-327 (May 2009).
Mazurek, B., et al., "Effect of short HV pulses on bacteria and fungi," IEEE Transactions on Dielectrics and Electrical Insulation, vol. 2, Issue 3, pp. 418-425 (Jun. 1995).
McCaughey, B., "Hospital Scrubs are a Germy, Deadly Mess," accessed at https://web.archive.org/web/20150224075518/http://www.wsj.com/articles/SB123137245971962641, updated on Jan. 8, 2009, pp. 3.
Mittal, G. S., "Non-thermal food processing with pulsed electric field technology," Resource, Engineering & Technology for a Sustainable World, vol. 16, No. 2 pp. 6-8 (Mar. 1, 2009).
Ng., W., and Piekarski, K., "The effect of an electrostatic field on the mitosis of cells," Medical and biological engineering, vol. 13, Issue 1, pp. 107-111 (Jan. 1975).
Nogueira, J.C.R., et al., "Identification and antimicrobial susceptibility of acute external otitis microorganisms," Brazilian Journal of Otorhinolaryngology, vol. 74, Issue 4, pp. 526-530 (Jul.-Aug. 2008).
Otunola, A., et al., "Effectiveness of Pulsed Electric Fields in Controlling Microbial Growth in Milk," International Journal of Food Engineering, vol. 4, Issue 7, p. 1 (Aug. 27, 2008).
Paulson, T., "Microwaving malaria and the other latest winners of Gates Foundation research grants," Humanosphhere, accessed at https://web.archive.org/web/20140902091739/http://www.humanosphere.org/science/2011/07/microwaving-malaria-and-the-other-latest-winners-of-gates-foundation-research-grants/, posted on Jul. 13, 2011, pp. 6.
Pedro, J. A. D., et al., "Pulsed electromagnetic fields induce peripheral nerve regeneration and endplate enzymatic changes," Bioelectromagnetics, vol. 26, Issue 1, pp. 20-27 (Jan. 2005).
Perni, S., et al., "Bacterial cells exposed to nanosecond pulsed electric fields show lethal and sublethal effects," International Journal of Food Microbiology, vol. 120, Issue 3, pp. 311-314 (Dec. 15, 2007).
Piatti, E., et al., "Antibacterial effect of a magnetic field on Serratia marcescens and related virulence to Hordeum vulgare and Rubus fruticosus callus cells," Comparative Biochemistry and Physiology Part B: Biochemistry and Molecular Biology, vol. 132, Issue 2, pp. 359-365 (Jun. 2002).
Pickering, SA., et al., "Electromagnetic augmentation of antibiotic efficacy in infection of orthopaedic implants," The Journal of Bone & Joint Surgery Br., vol. 85, Issue 4, pp. 588-593 (May 2003).
Pilla, A. A., "Mechanisms and Therapeutic Applications of Time-Varying and Static Magnetic Fields," Handbook of Biological Effects of Electromagnetic Fields, 3rd Edition. Barnes F, Greenebaum B, eds, CRC Press, 2006, pp. 1-79 (2006).
Pina-Pérez, M. C., et al., "Synergistic effect of Pulsed Electric Fields and CocoanOX 12% on the inactivation kinetics of Bacillus cereus in a mixed beverage of liquid whole egg and skim milk," International Journal of Food Microbiology, vol. 30, Issue 3, pp. 196-204 (Apr. 15, 2009).

(56) References Cited

OTHER PUBLICATIONS

Pizzichemi, M., "Interaction of pulsed electric fields with cell membrane," (Doctoral dissertation, University of Milan-Bicocca, Anno Accademico, pp. 1-163 (2008-2009)—in 2 Parts due to size of file.
Raso, J., et al., "Improvement winemaking by pulsed electric fields," accessed at https://web.archive.org/web/20110510145249/http://www.scitopics.com/Improvement_winemaking_by_pulsed_electric_fields.html, published on Mar. 23, 2010, pp. 4.
Sale, A. J. H., and Hamilton, W. A., "Effects of high electric fields on microorganisms: I. Killing of bacteria and yeasts," Biochimica et Biophysica Acta (BBA)—General Subjects, vol. 148, Issue 3, pp. 781-788 (Dec. 27, 1967).
Sanders, B., "Protozoa and UV Radiation," accessed at http://www.orgs.miamioh.edu/uvlakes/UVecology/Protist/protozoa.html, accessed on Apr. 13, 2015, pp. 2.
Santos, F., et al., "Methicillin-resistant *Staphylococcus aureus*: pediatric otitis," Archives of otolaryngology head & neck surgery, vol. 126, Issue 11, pp. 1383-1385 (Nov. 1, 2000).
Schoenbach, K. H., et al., "Bacterial decontamination of liquids with pulsed electric fields," IEEE Transactions on Dielectrics and Electrical Insulation, vol. 7, Issue 5, pp. 637-645 (Oct. 2000).
Shamis, Y., et al., "Specific Electromagnetic Effects of Microwave Radiation on *Escherichia coli*," Applied and Environmental Microbiology, vol. 77, No. 9, pp. 3017-3022 (May 2011).
Spilimbergo, S., et al., "Inactivation of bacteria and spores by pulse electric field and high pressure CO2 at low temperature," Biotechnology and Bioengineering, vol. 82, Issue 1, pp. 118-125 (Apr. 5, 2003).
Stolfa, S., et al., "Effects of static magnetic field and pulsed electromagnetic field on viability of human," Physiol. Res. 56 (Suppl. 1), vol. 56, pp. S45-S49 (May 31, 2007).
Strange, P., et al., "Staphylococcal Enterotoxin B Applied on Intact Normal and Intact Atopic Skin Induces Dermatitis," Arch Dermatol, vol. 132, Issue 1, pp. 27-33 (Jan. 1, 1996).

Strauch, B., et al., "Evidence-Based Use of Pulsed Electromagnetic Field Therapy in Clinical Plastic Surgery," Aesthetic Surgery Journal, vol. 29, No. 2, pp. 135-143 (Mar./Apr. 2009).

Tomanek, L., and Somero, GN., "Time course and magnitude of synthesis of heat-shock proteins in congeneric marine snails (Genus *Tegula*) from different tidal heights," Physiol Biochem Zool., vol. 73, Issue 2, pp. 249-256 (Mar.-Apr. 2000).

Toshkova, K., et al., "The significance of nasal carriage of *Staphylococcus aureus* as risk factor for human skin infections," FEMS Microbiology Letters, vol. 202, Issue 1, pp. 17-24 (Aug. 7, 2001).

Tovmasian, V. S., et al., "Effect of an electrostatic field on the synthesis of antibodies," Zhurnal Eksperimental Klinicheskoi Meditsiny, vol. 16, Issue 5, pp. 42-44 (1976).

Tudor, T. L, "Overcoming attitudes and perceptions towards the management of infections and waste in the hospital setting: a case study from the UK," International Journal of Behavioural and Healthcare Research, vol. 2, No. 4, pp. 307-319 (Oct. 31, 2011).

Ulbrich, L.M., et al., "Prototype development to expose bacterial cultures to magnetic fields," Perspectives in Oral Sciences, vol. 2, No. 1, pp. 33-37 (Apr. 2010).

Umarov, GR, et al., "Effect of electrostatic field on bacteria *E. coli*," Aviakosm Ekolog Med., vol. 33, Issue 1, pp. 61-62 (1999).

Vavken, P., et al., "Effectiveness of pulsed electromagnetic field therapy in the management of osteoarthritis of the knee: a meta-analysis of randomized controlled trials," Journal of Rehabilitation Medicine, vol. 41, Issue 16, pp. 406-411 (May 2009).

Ventura, A., et al., "The effect of bacterial infection in the worsening of atopic dermatitis: correlations with humoral immunologic patterns," Annals of allergy, vol. 63, Issue 2, pp. 121-126 (Aug. 1989).

Vouloumanou, E. K., et al., "Antibiotics versus placebo or watchful waiting for acute otitis media: a meta-analysis of randomized controlled trials," Journal of Antimicrobial Chemotherapy, vol. 64, Issue 1, pp. 16-24 (May 19, 2009).

Walker, N. A., et al., "Low-Intensity Pulsed Ultrasound and Pulsed Electromagnetic Field in the Treatment of Tibial Fractures: A Systematic Review," Journal of Athletic Training, vol. 42, Issue 4, pp. 530-535 (Oct.-Dec. 2007).

Walshe, P., et al., "A worrying development in the microbiology of otitis externa," Clinical Otolaryngology & Allied Sciences, vol. 26, Issue 3, pp. 218-220 (Jun. 2001).

Warwicker, J., et al., "Electrostatic field of the large fragment of *Escherichia coli* DNA polymerase I," Journal of Molecular Biology, vol. 186, Issue 3, pp. 645-649 (Dec. 5, 1985).

Weintraub, MI., et al., "Pulsed electromagnetic fields to reduce diabetic neuropathic pain and stimulate neuronal repair: a randomized controlled trial," Arch Phys Med Rehabil vol. 90, Issue 7, pp. 1102-1109 (Jul. 2009).

Yaeger, R. G., "Protozoa: Structure, Classification, Growth, and Development," Medical Microbiology, 4th edition, Chapter 77, pp. 1-8 (1996).

Yeom, H. W., et al., "Effects of Pulsed Electric Fields on the Activities of Microorganisms and Pectin Methyl Esterase in Orange Juice," Journal of Food Science, vol. 65, Issue 8, pp. 1359-1363 (Nov. 2000).

Yu, LH., et al., "Malignant otitis externa," Zhonghua yi xue za zhi, vol. 62, Issue 6, pp. 362-368 (Jun. 1999).

Zhang, S., et al., "Effect of static magnetic field on growth of *Escherichia coli* and relative response model of series piezoelectric quartz crystal," Analyst, vol. 127, Issue 3, pp. 373-377 (Mar. 2002).

Zorzi, C., et al., "Effects of pulsed electromagnetic fields on patients' recovery after arthroscopic surgery: prospective, randomized and double-blind study," Knee Surg Sports Traumatol Arthrosc, vol. 15, Issue 7, pp. 830-834 (Jul. 2007).

International Search Report PCT/US2012/033923, dated Aug. 27, 2012.

Bogomol'Skiĭ, M.R., et al., "Cerumenolysis in neonates and babies," Vestn Otorinolaringol., vol. 4, pp. 90-92 (2010).

Campos, A., et al., "Influence of human wet cerumen on the growth of common and pathogenic bacteria of the ear," The Journal of Laryngology & Otology, vol. 114, Issue 12, pp. 925-929 (Dec. 2000).

Chambers, H. F. III, and Winston, L. G., "Mupirocin Prophylaxis Misses by a Nose," Annals of Internal Medicine, vol. 140, Issue 6, pp. 484-485 (Mar. 16, 2004).

Dawson, D.A., "Malignant otitis externa", The Journal of Laryngology & Otology, vol. 92, Issue 9, pp. 803-810 (Sep. 1, 1978).

International Search Report and Written Opinion for International Application No. PCT/US2013/057850, dated Feb. 10, 2014, pp. 13.

Rosso, J.Q. and Elston, D.M., "Tackling the anterior nares and other sites of colonization: implications for the dermatologist," Cutis, vol. 79, No. 6 Suppl., pp. 52-59 (Jun. 2007).

Klien, J. and Chan, S., et al., "Methicillin-Resistant *Staphylococcus aureus* in Middle Ear Fluid of Children," Clin Pediatr (Phila)., vol. 49, No. 1, pp. 66-68 (Jan. 2010).

Park, C., et al. "An analysis of the bacterial flora found in the external auditory canals of microtia patients: results and alinical applications," Ann Plast Surg., vol. 65, Issue 2—pp. 197-200 (Aug. 2010).

Stone, A., et al., "*Staphylococcus aureus* nasal colonization among pediatric cystic fibrosis patients and their household contacts," Pediatric Infectious Disease Journal, vol. 28, No. 10, pp. 895-899 (Oct. 2009).

* cited by examiner

HEAT TREATMENT DEVICE

CROSS-REFERENCE TO RELATED APPLICATIONS

This application is a U.S. National Phase under 35 U.S.C. § 371 of International Application PCT/US2012/033923, filed Apr. 17, 2012, which designated the U.S. and which is hereby expressly incorporated by reference in its entirety.

BACKGROUND OF THE INVENTION

Applying heat to the site of an infection or other condition can be an effective form of treatment. Current heat treatments may involve application of warm compresses or other devices that have difficulties applying a precise, regulated temperature to the entire site of treatment.

SUMMARY OF THE INVENTION

Thermal based treatments can be designed for use in treating a variety of conditions. Certain advantageous embodiments disclosed herein reduce or eliminate various problems associated with current thermal devices or non-thermal treatments such as the use of antibiotics for treating certain infections. For example, using antibiotics is subject to potential disadvantages of bacterial resistance, allergic reactions, drug interactions, limited topical application, patient compliance, and other limitations. Additionally, thermal treatments can be used not only to treat external infections and opened, internal infections, but also to prevent infection by applying controlled heat to a wound. This can help limit infections during surgery if heat is applied before and/or immediately after surgical closure. Further, thermal treatments can be used for a variety of non-infectious conditions, such as to accelerate wound healing or treat skin cracks, tendinitis, pressure sores, alopecia, or ulcers, to name but a few examples.

Different treatments may be improved by use of different embodiments of a heat treatment device. Some treatments can benefit from embodiments comprising a rigid tip that can allow for precise application of heat. Other treatments can benefit from embodiments comprising conformable tips that can mold to specific contours of a treatment area. In some embodiments of a heat treatment device an application tip can maintain a regulated temperature across the contact surface, even as heat flows into the treatment area.

According to some embodiments a heat treatment device can comprise a body comprising a handle portion and a tip portion. The device can further comprise a power source and at least one heating element in electrical communication with the power source and configured to heat the tip portion to a desired temperature. The tip portion can be placed against an affected area for treatment. The device can comprise control circuitry configured to adjust a current flowing to the heating element when the device is in use to maintain the tip portion at the desired temperature. The tip portion can be heatable to a desired temperature and positioned against the affected area for treatment.

In some embodiments, a heat treatment device can further comprise a pressure sensor configured to measure a force applied by the tip portion against the affected area and to provide a feedback signal to a physician that indicates the force measured by the pressure sensor. In some embodiments, the at least one heating element can be disposed within the tip portion. In some embodiments, the heating element can be disposed within the handle portion. In some embodiments, the at least one heating element is a resistive heating element, and in further embodiments the control circuitry can be configured to measure the temperature by sampling a resistance of the resistive heating element.

In some embodiments, the tip portion can comprise a tip housing, and the at least one heating element can be disposed at least partially within the tip housing and extend from a distal end of the tip. In further embodiments, the tip portion can comprise a temperature sensor in electrical communication with the control circuitry in order to maintain the tip portion at the desired temperature.

In some embodiments, the device can be modular such that the tip portion is separable and removable from the body to allow a replacement tip portion to be mounted onto the body after the tip portion is removed. In some embodiments, the body can comprise a connector portion configured to be coupled with a respective connector portion of the tip portion. In further embodiments, the replacement tip portion can comprise an electronic identifier that is recognizable by the control circuitry, and the control circuitry can be configured to adjust the current flowing to the at least one heating element of the replacement tip portion when the device is in use in response to the electronic identifier of the replacement tip portion.

In some embodiments, a heat treatment device can comprise a body comprising a handle portion, a tip portion coupled to the handle portion, and a fluid channel extending through the handle portion to the tip portion such that the handle portion is in fluid communication with the tip portion. The device can further comprise a power source supported by the body and at least one heating element disposed in the handle portion, the at least one heating element in electrical communication with the power source such that the at least one heating element is configured to heat a fluid disposed within the fluid channel. The device can further comprise a pump supported by the handle portion, the pump configured to urge fluid through the fluid channel from the handle portion toward the tip portion of the device, and control circuitry supported by the body of the device, the control circuitry configured to adjust a current flowing to the at least one heating element when the device is in use. The device can also be configured such that the at least one heating element heats a fluid disposed in the fluid channel of the handle portion, and the pump can be configured to facilitate transfer of the fluid toward the tip portion of the device to heat the tip portion to a desired temperature.

In some embodiments, a heat treatment device can further comprise a return fluid channel extending from the tip portion toward the handle portion, the return fluid channel in fluid communication with the fluid channel, forming a circulatory pathway to allow fluid to be circulated within the device.

In some embodiments, the tip portion can comprise a conformable material. In some embodiments, the tip portion can comprise a temperature sensor in electrical communication with the control circuitry for maintaining the tip portion at the desired temperature.

In some embodiments, the handle portion can comprise a first chamber with a first heating element and a second chamber with a second heating element. The first chamber can be configured to heat the fluid in the first chamber to a first temperature below the desired temperature, and the second chamber can be configured to heat the fluid in the second chamber to a second temperature greater than the first temperature. In some embodiments, the first chamber and the second chamber can be in fluid communication with the fluid channel.

In some embodiments, the device is modular such that the tip portion is separable and removable from the body to allow a replacement tip portion to be mounted onto the body after the tip portion is removed. In further embodiments, the body comprises a connector portion configured to be coupled with a respective connector portion of the tip portion. In yet further embodiments, the replacement tip portion comprises an electronic identifier that is recognizable by the control circuitry, the control circuitry being configured to adjust the current flowing to at least one heating element when the device is in use in response to the electronic identifier of the replacement tip portion.

In some embodiments, a replaceable tip portion for a heat treatment device for therapeutically treating an affected area of a patient using heat can comprise a connector portion comprising an inlet flow path and an outlet flow path, the connector portion configured to engage with a respective connector portion of the heat treatment device for mounting the replaceable tip portion on the heat treatment device and fluidly interconnecting the inlet flow path with a respective device fluid source and the outlet flow path with a device fluid receptacle. The replaceable tip portion can further comprise a contacting portion positioned adjacent to at least a portion of the inlet flow path for facilitating the thermal transfer from a fluid to an external surface of the contacting portion to enable heat treatment of an affected area by placing the contacting portion thereagainst. The replaceable tip portion can be replaceably mounted onto the heat treatment device for performing heat therapy on the affected area.

In some embodiments, an external surface of the contacting portion can comprise a conformable material. In further embodiments, the external surface of the contacting portion can comprise a rigid material. In yet further embodiments, the inlet flow path of a replaceable tip portion can comprise a single flow path that splits into a plurality of flow paths within the contacting portion.

In some embodiments, a replaceable tip portion for a heat treatment device for therapeutically treating an affected area of a patient using heat can comprise a connector portion and a contacting portion, the connector portion configured to engage with a respective connector portion of the heat treatment device for mounting the replaceable tip portion on the heat treatment device, and a heating element in thermal communication with the contacting portion and in electrical communication with the connector portion for heating the contacting portion to a desired temperature. The replaceable tip portion can be mounted onto the heat treatment device for performing heat therapy on the affected area.

In some embodiments, the replaceable tip portion can further comprise a conducting element that extends through the replaceable tip portion and is electrically coupled with the connector portion and the heating element. In further embodiments, the replaceable tip portion can comprise a connector jacket that is engageable with and removable from the connector portion, and a tip jacket that is engageable with and removable from the contacting portion. The connector jacket and the tip jacket can attach to the replaceable tip portion for preserving sterility of the replaceable tip portion when disengaged from the heat treatment device.

In some embodiments, the contacting portion of the replaceable tip portion can comprise a conformable material. In some embodiments, the contacting portion can comprise a tip housing at least partially surrounding a contacting tip of the contacting portion, and the tip housing can comprise a thermally conductive and electrically insulating plastic.

In some embodiments, treatment of an affected area of a patient with heat can comprise allowing a tip of a heat applicator device to reach a desired temperature of about 105 degrees Fahrenheit to about 140 degrees Fahrenheit, applying the tip against the affected area at an applied pressure, maintaining the tip against the affected area for a therapeutically effective period of time, and removing the tip from against the affected area of the patient. In some embodiments, treatment can further comprise measuring the applied pressure using the applicator to determine whether the applied pressure is within a target pressure range and adjusting the applied pressure as needed such that the applied pressure is within the target pressure range.

In some embodiments, treatment can comprise heating the affected area until the affected area reaches a temperature of about 105 degrees Fahrenheit to about 140 degrees Fahrenheit. In some embodiments, treatment can further comprise determining an actual temperature of the tip of the applicator and adjusting an amount of energy provided to the tip such that the actual temperature is approximately equal to the desired temperature.

In some embodiments, the tip can comprise a resistive heating element, and determining the actual temperature of the tip can comprise measuring a resistance of the resistive heating element and determining a temperature that corresponds to the measured resistance. In some embodiments, determining the actual temperature of the tip can comprise measuring the actual temperature using a temperature sensor positioned proximate to the tip. In some embodiments, the applicator can further comprise a controller configured to increase or decrease of the amount of energy supplied to the tip.

In some embodiments, allowing the tip of the heat applicator device to reach a desired temperature can be performed after the tip is applied to the affected area. In further embodiments, the tip of the heat applicator device can reach a desired temperature after it has been applied to the affected area for at least about 5 seconds. In some embodiments, after the tip of the heat applicator has been applied to the affected area, it can be heated at a first rate and then heated at a second rate, the second rate greater than the first rate.

In some embodiments, treatment of an affected area of a patient with heat can comprise selecting a tip portion for the heat treatment device from a plurality of tip portions, each having a unique size, such that the size of the tip portion is selected to generally correspond to the width of the affected area. The tip portion can comprise a first connector, and the first connector can be connected to a second connector of a body portion of the heat treatment device. The tip portion can be heated to a desired temperature and positioned against the affected area, thereby thermally treating the affected area.

In some embodiments, treatment can comprise heating the affected area until the affected area reaches a temperature of about 105 degrees Fahrenheit to about 140 degrees Fahrenheit. In some embodiments, treatment can further comprise determining an actual temperature of the tip of the applicator and adjusting an amount of energy provided to the tip in order to maintain the actual temperature approximately equal to the desired temperature.

In some embodiments, determining the actual temperature of the tip can comprise measuring a resistance of a heating element and determining the actual temperature based on the measured resistance. In some embodiments, determining the actual temperature of the tip can comprise measuring the actual temperature using a temperature sensor disposed proximate to a heating element of the tip portion. In some embodiments, the applicator can further comprise a controller that automatically effects the increase or decrease of the amount of energy supplied to the heating element.

In some embodiments, treatment can comprise determining an applied pressure of the tip portion against the affected area and adjusting the applied pressure such that the applied pressure is within a target pressure range. In further embodiments, treatment can comprise adjusting the applied pressure in response to a feedback signal generated from the heat treatment device.

In some embodiments, a heat treatment system for therapeutically treating an affected area of a patient using heat can comprise a handle portion, a tip portion coupled to the handle portion, a fluid channel extending through the handle portion to the tip portion such that the handle portion is in fluid communication with the tip portion, a power source supported by the handle portion and electrically connected to at least one heating element such that the at least one heating element is configured to heat a fluid disposed within the fluid channel for heating the tip portion to a desired temperature, and control circuitry supported by the body of the device, the control circuitry configured to adjust a current flowing to the at least one heating element when the device is in use. The system can further comprise a base station comprising a power connection and a fluid connection, the power connection configured to recharge the power source of the heat treatment device, the fluid connection interconnectable with the heat treatment device to provide fluid to the fluid channel of the heat treatment device.

In some embodiments, the base station of a heat treatment system can be configured to charge the power source through inductive charging. In some embodiments, the base station can be a wheeled cart. In some embodiments, the base station can further comprise a drain and a connection to an external water source. In further embodiments, the heat treatment device can be modular such that the tip portion is separable and removable from the body to allow a replacement tip portion to be mounted onto the body after the tip portion is removed.

DETAILED DESCRIPTION

Figure 1:
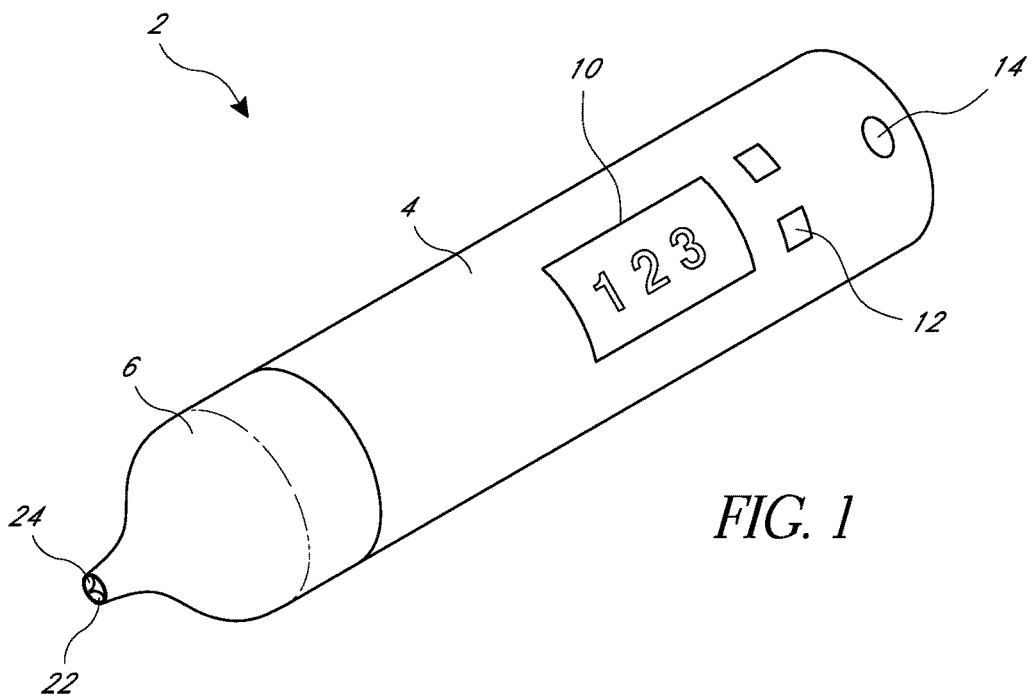
FIG. 1 is a perspective view of a solid state embodiment of a heat treatment device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This description relates generally to heat treatment devices that have a heatable tip configured to maintain a desired temperature when placed in contact with a treatment surface. In some embodiments, the heat treatment device can be a solid-state heat treatment device in which the tip of the device conducts heat directly from a heater. In some embodiments, the heat treatment device can be a liquid heat treatment device, in which the device can have a circulating fluid that transfers heat from a heater to the tip.

FIG. 1 illustrates one embodiment of a solid-state heat treatment device 2. The illustrated embodiment has a handle 4 at a proximal end of the device and a tip portion 6 located at a distal end of the device. The tip 6 of the device can have one or more sensors at a distal end. For example, in the illustrated embodiment, the tip can have a temperature sensor 22 and a pressure sensor 24. In other embodiments, the tip can have just a temperature sensor, just a pressure sensor, different sensors, or no sensors.

The distal end of the tip 6 can have a variety of shapes, depending on the treatment to be performed. The distal end can be flat, rounded, or of other shapes or combinations of shapes. In some embodiments, the distal end that contacts a patient can define a diameter of 2 mm to about 10 mm. In some embodiments, the distal end can define a diameter of less than 2 mm or more than 10 mm. In some embodiments, the distal end can define a surface area of about 10 mm$^2$ to about 400 mm$^2$. In further embodiments, the distal end can define a surface area of about 20 mm$^2$ to about 300 mm$^2$. In further embodiments, the distal end can define a surface area of about 50 mm$^2$ to about 200 mm$^2$. In yet further embodiments, the distal end can define a surface area of less than 10 mm$^2$ or more than 400 mm$^2$.

In the illustrated embodiment, the tip has a concave surface at the distal end that can be useful when treating sties or other conditions that are elevated relative to the surface of a patient's skin. A concave surface can help increase the contact surface between the area to be treated and the tip, without the need to apply excessive pressure. A force or pressure sensor 24 can be used to detect the contact force or pressure, and the device can emit a visual or audio signal to guide the physician or user of the device. In some embodiments, the signal can be set to trigger when the applied pressure or force exceeds a threshold pressure or force. In other embodiments, the signal can trigger when the applied pressure or force falls below a threshold pressure or force. In further embodiments, a first signal can trigger when the applied pressure or force exceeds a first value, and a second signal can trigger when the applied pressure or force falls below a second value.

The handle can have a display 10, which can be used in various embodiments to display the temperature at the tip, the treatment time, the applied force or pressure, or other variables of interest. The handle can also have a plurality of user interface buttons 12. The buttons can be used to turn on and turn off the device, to set and control the temperature, to set a treatment time, or to set and control other parameters. The device can also have one or more indicator lights 14. The indicator lights can a single color or can be capable of displaying multiple colors. The indicator lights can inform a user when the device is turned on, when the force or pressure exceeds or falls below a predetermined force or pressure, when the temperature exceeds or falls below a predetermined temperature, when a predetermined treatment time has occurred, or when other set conditions have been met. The handle can also have a noise-emitter or speaker (not shown) that can be used in conjunction with or in place of the indicator lights.

Figure 2:
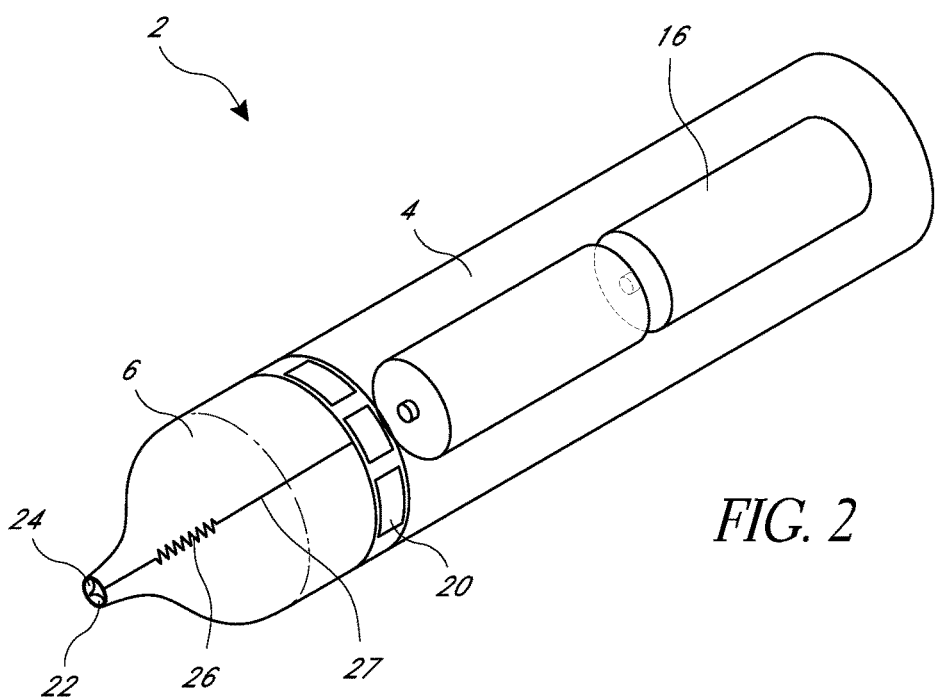
FIG. 2 is an internal perspective view of the device of FIG. 1.

FIG. 2 illustrates an internal perspective view of one embodiment of the heat treatment device. The device may have a power source 16 disposed within the handle of the device. As illustrated, the power source can have one or more rechargeable batteries. The one or more batteries can be nickel metal hydride, lithium ion, nickel cadmium, or any other type of battery known in the art. The power source can power control circuitry 20, may be disposed within the handle of the device but which in some embodiments can be disposed within the tip, and heating element 26. Heating element 26 can be in electrical communication with the power source 16 by means of a wire 27 or other conductive element. The heating element may be a resistive heating element, such as nichrome wire. Although discussed in the context of a single heating element, in some embodiments the device can have one or more heating elements.

The control circuitry 20 can be configured to communicate with any sensors attached to the device, to control the power to the heating element, to control any indicator lights and/or sounds, and to otherwise control the operation of the device. The control circuitry may have at least a proportional-integral-derivative controller. In embodiments where the tip has a temperature sensor, the control circuitry can receive temperature measurements from the temperature sensor and adjust power delivery to maintain the tip at a desired temperature. In other embodiments, because resistance generally varies with temperature, the control circuitry can measure the temperature by pulsing current to the heating element and sampling resistance during off phases. In further embodiments, the device can have additional electronic components that can be configured to record data from the procedure, such as, for example, the particular tip used, the treatment temperature, the treatment time and date, the applied pressure, or any other desired variables. The device can also have an input or form of wireless communication that can allow a user to download recorded information.

Figure 3:
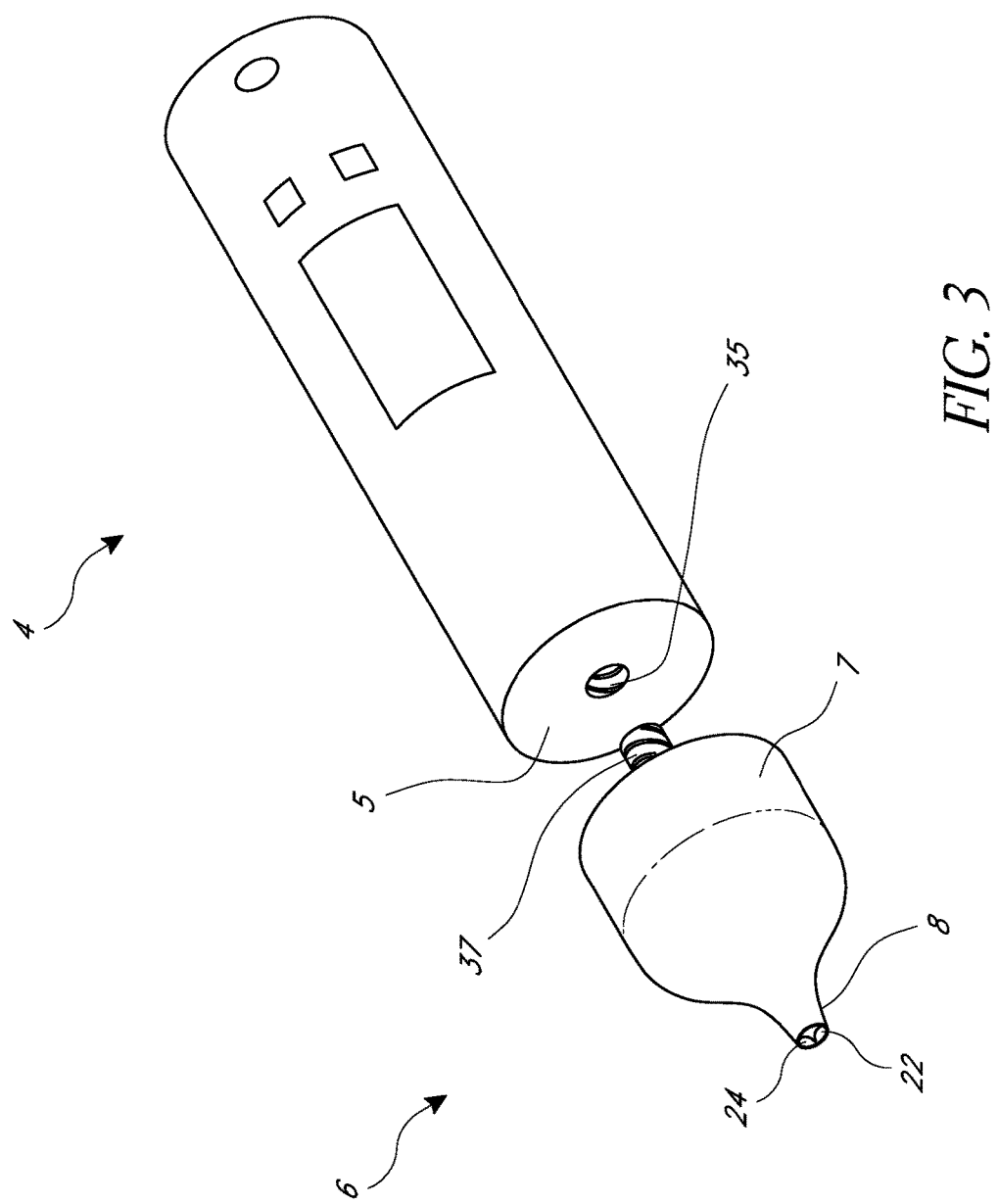
FIG. 3 is a perspective view of a solid state embodiment of the heat treatment device in which the tip is removable from the handle.

In some embodiments, the tip 6 and handle 4 can be integrated together. In some embodiments, the tip and handle can be modular pieces, capable of replacement with interchangeable parts or components, as illustrated in FIG. 3. Embodiments where the tip and handle are modular allows for use of separate tips for separate patients or conditions, and also for using tips of varying sizes and distal geometry for more precise treatment of infections or other conditions. For example, when treating sties, it can be beneficial to have the diameter of the distal end of the tip approximately matching the size of the sty. Further, as discussed above, it can be advantageous to have a concave surface at the distal end of the tip when treating sties, but when treating other infections or conditions it can be beneficial to have a rounded portion or other shape at the distal end of the tip.

As illustrated in FIG. 3, the tip 6 and the handle 4 can be configured to releasably attach to each other. In some embodiments, the tip can have a connector portion 7 and a contacting portion 8. The tip can have a connector 37 on a proximal surface of the connector portion 7 of the tip, and the handle can have a connector 35 along a distal surface 5 of the handle. As illustrated, the connector 37 of the tip is a male connector that is received by a female connector 35 of the handle. In other embodiments, the handle can have a male connector and the tip can have a female connector. The connectors can provide an electrical connection between the heating element of the tip and the control circuitry and power source disposed within the handle. Further, the connectors can be threaded and configured such that the male connector can screw into the female connector, creating a secure but releasable connection. In alternate embodiments, the tip and the handle can have one or more latch mechanisms that allow the tip to be quickly and easily secured to the handle while also allowing quick and easy removal of the tip from the handle. In further embodiments, the heat treatment device can have a second connector on the handle that can connect via an electrical cable to a second tip.

Figure 4:
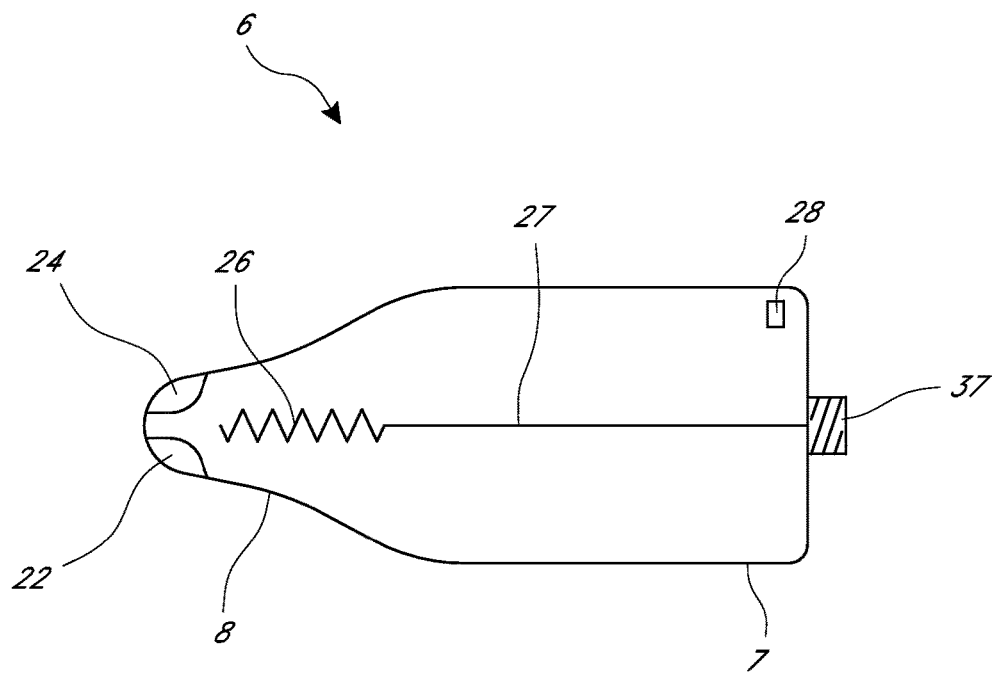
FIG. 4 is a side cross sectional view of one embodiment of a replaceable tip.

FIG. 4 illustrates a cross-sectional view of one embodiment of the tip 6. As illustrated, the tip has a heating element 26 and a wire 27 connecting the heating element to the connector 37 of the tip. Other forms of electrical connection may be used to connect the heating element 26 to the connector 37 of the tip, and through the connector to the power source disposed within the handle of the device. The heating element 26 within the contacting portion of the tip can be surrounded by a tip housing or outer surface, which may have a thermally conductive and electrically insulating material such as certain plastics.

Because some embodiments of the tip can have a heating element of different sizes and/or resistances, and in some embodiments the tip can be of varying shapes and materials, it can be beneficial for the power source to apply differing amounts of power to a particular tip in order yield a desired temperature at the contacting portion 8 of the tip. In some embodiments, a user of the device can manually enter the tip selected. In other embodiments, the control circuitry can be configured to recognize a particular tip that has been attached to the handle of the device. This can be accomplished in some embodiments by having the control circuitry measure the resistance of the tip prior to delivering power to the tip for purposes of treating a patient. In other embodiments, the tips can have an electronic identifier 28 which can inform the control circuitry of the particular tip. In further embodiments, the tip can have a group of optically reflective dots or stripes along its proximal surface, and the handle can have photo emitters/detectors along its distal surface that can read a particular arrangement of dots and/or stripes on the tip that correspond to a particular tip design.

Figure 5:
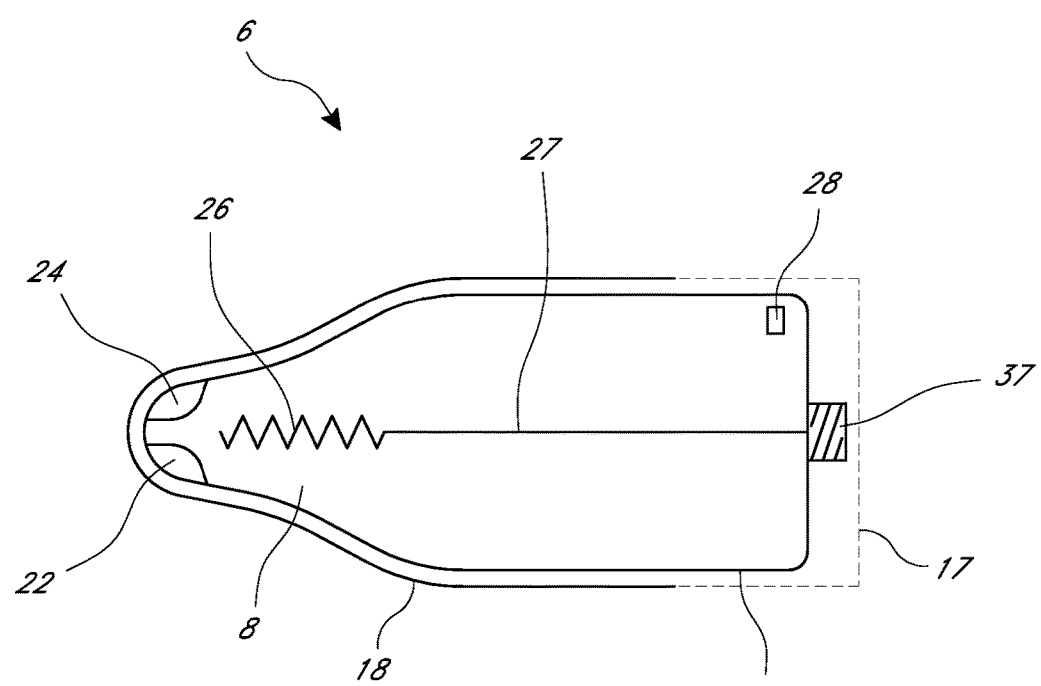
FIG. 5 is a side cross sectional view of the embodiment of FIG. 4 with a protective sleeve around it.

In addition to being modular, the tips can also be disposable. To ensure sterility of the tips, they can be shipped and stored in sterile packaging. The embodiment illustrated in FIG. 5 is one way to store the tip in the sterile package and yet allow for easy removal of the package and installation of the tip onto the handle of the device. The package can have a first part 17 surrounding at least a part of the connector portion of the tip and a second part 18 surrounding at least a part of the contacting portion of the tip. The first part 17 is illustrated as a dashed line for clarity. The first and second parts of the cover are releasably attached to each other such that one portion can be removed and thrown away while the other portion remains around the tip. For example, the first portion 17 around at least a part of the connector portion of the tip can be pinched and removed with one hand while a physician or user of the device holds the contacting portion of the tip, which is still protected by the second part 18 of the cover. The user can connect the exposed tip to the handle of the device and then remove the second part 18 while holding onto the handle of the device. This exposes the contacting portion of the tip, which is now connected to the handle, for application on a patient without having introducing any pathogens to the tip portion from contact with the physician or user's hands.

The contacting portion of a heat treatment device—both the solid-state heat treatment device discussed above and the liquid heat treatment device discussed below—can be maintained at a predetermined temperature between 105 degrees Fahrenheit plus or minus five degrees and 140 degrees Fahrenheit plus or minus five degrees when applied against a patient. In some embodiments the contacting portion can be maintained at a temperature below 105 degrees Fahrenheit—in other embodiments it can be maintained above 140 degrees Fahrenheit. Certain infections or conditions may be more responsive to specific temperatures, so the precise treatment temperature frequently depends on the particular condition to be treated. For example, a desired temperature for treating internal sties in some embodiments can be between approximately 115 and 120 degrees Fahrenheit. A desired temperature for treating external sties in some embodiments can be between approximately 125 and 130 degrees Fahrenheit. Additionally, conditions generally respond positively not to a precise temperature but to a therapeutic range of temperatures. Treatment at a lower temperature within a therapeutic range can be just as effective, but may require a longer treatment time.

In some embodiments, at least for applications that treat infections, the treatment temperature can be sufficiently high to neutralize, kill, or otherwise inactivate the bacteria or infectious agent. In some embodiments, e.g., for treatment of tumors, cancer, and both benign and malignant skin cancer (e.g., melanoma), etc., local hyperthermia may provide treatment temperatures that are sufficiently high to kill the cancer cells and/or to render the cancer cells more susceptible to chemotherapy or radiation therapy and/or to enhance the patient's immune response against the cancer cells.

The treatment temperature can also depend on the external temperature of the patient's skin, which can affect the rate of heat transfer. In some embodiments, in order to enhance heat transfer from the tip to the patient's tissue, a thermally conductive gel can be administered to the treatment site prior to applying the tip. In some embodiments, the tip can be heated to the desired temperature and then applied to the treatment site. In other embodiments, discussed in more detail below, patient discomfort can be minimized by applying the tip of the device to the treatment site before the tip has reached the desired treatment temperature. In some embodiments, in order to ensure precise placement of the tip such that substantially only the desired treatment areas receive heat, the device can have a locator element disposed adjacent the tip portion and that can provide a visual indication on the affected area. For example, in some embodiments the locator element can have a fiber optic filament in communication with a light source for transmitting a light beam onto the affected area.

Treatment times—for both the solid-state heat treatment device discussed above and the liquid heat treatment device discussed below—can vary depending on the treatment temperature and the particular condition to be treated. For the same treatment temperature, the treatment time can be longer or shorter depending on the condition to be treated and/or the size of the particular condition. For the same treatment condition, the treatment time can be longer or shorter depending on the treatment temperature: for a treatment temperature at a lower end of a therapeutic range a longer treatment time is generally desired; similarly, a shorter treatment time is generally desired for a treatment temperature at a higher end of a therapeutic range. In some embodiments, the treatment time can be between approximately 0 and 10 seconds. In some embodiments, the treatment time can be between 10 and 20 seconds. In further embodiments, the treatment time can be between 20 and 40 seconds, between 40 and 60 seconds, between 60 and 80 seconds, or greater than 80 seconds.

As an example, when treating a chalazion, thermal liquification of the hardened oil in the eyelid gland is one of the therapeutic effects. In an experimental application, this therapeutic effect was achieved by applying a tip at 119 degrees Fahrenheit against a chalazion for approximately 20 seconds. In a subsequent application, the same therapeutic effect was achieved on a different chalazion at a tip temperature of 111 degrees Fahrenheit applied for approximately 70 seconds. In other experimental applications, application of a tip at approximately 135 degrees Fahrenheit to cracks in fingertip skin for approximately 90 seconds succeeded in accelerating wound healing.

In general, experimental application of a heat treatment device to sties, chalazia, and skin cracks was therapeutically effective in that it greatly accelerated complete resolution of the conditions. In addition, heat treatment provided almost immediate reduction in pain and marked resolution of hallmarks of infection (e.g. pain, tenderness, redness, and swelling) and related symptoms (e.g., excessive tearing) within 24 hours. The slowest response was with skin cracks, which showed some healing within a few days and complete healing in about 5-7 days, which is substantially less than the time required for healing without heat treatment, which can be at least 2 weeks and often a month or more.

In some embodiments treatment is not constant but can be applied in a pulsatile manner. For example, the device can be applied against a treatment area for between approximately 1 to 5 seconds, and then be removed from the treatment area for between approximately 2 to 6 seconds. In some embodiments, the pulsed application time can be for less than 1 second or greater than 5 seconds. In some embodiments, the removal time during a pulsed application can be less than 2 seconds or greater than 6 seconds. In some embodiments, the control circuitry can be used to calculate subsurface temperatures and can generate a signal to stop treatment when a desired subsurface temperature at a desired treatment depth is reached.

Figure 6:
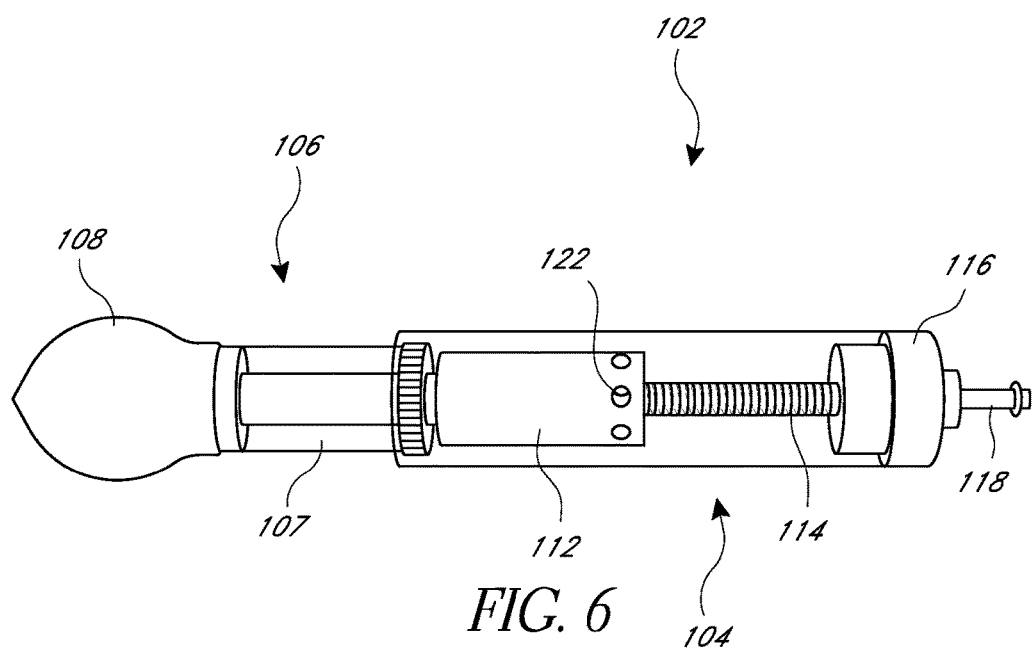
FIG. 6 is a side view of one embodiment of a liquid heat treatment device.

In some embodiments, rather than using an electrical current to deliver heat to the contacting portion of the tip, the device can rely on liquid or a fluid (the terms are used interchangeably in this application) to transfer heat to the contacting portion of the tip. FIG. 6 illustrates one embodiment of a liquid heat treatment device 102. The device functions generally by receiving water (e.g. tap water, distilled water, or a saline solution) or other liquid through a fill tube 118, attached to the handle of the device 104. The fill tube can be sealed. The fill tube can also be opened to allow water to drain from the device. In some embodiments the fill tube can have two channels, a first channel for receiving a liquid and a second channel for draining a liquid. A pump (not shown) located in housing 112 draws the fluid through inlets 122 into the pump housing 112. The fluid can receive some energy from a supplementary heater 114 and, once within the pump housing 112, the fluid can receive further energy from a heater (not shown) located within the housing. The fluid then passes to the tip 106 and circulates into a contacting portion of the tip 108, where it can pass heat through the tip to the tissue of a patient. The fluid then cycles back through the connector portion 107 of the tip and into the handle 104 of the device. Once back in the handle, the fluid passes into the pump housing 112 where it is heated again and returns to the tip 106.

In other embodiments of the liquid heat treatment device 102, certain elements can be arranged differently or can be excluded from the device altogether. The device generally contemplates all components and arrangements that have a fluid that receives heat, passes heat to the patient, and then cycles through the device to receive more heat.

Figure 7:
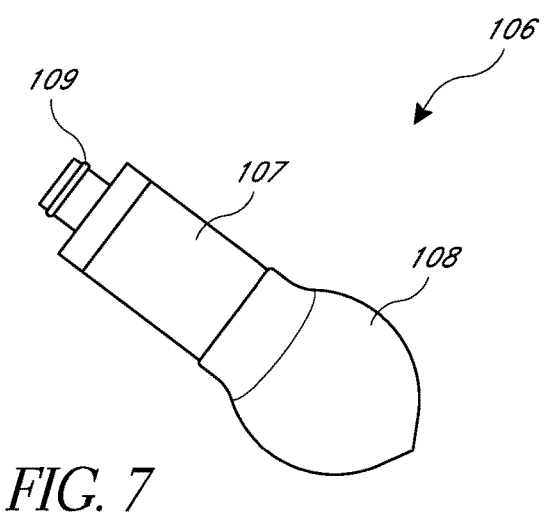
FIG. 7 is a side view of one embodiment of a replaceable tip for use with a liquid heat treatment device.

As with the solid-state heat treatment devices, the tips of liquid heat treatment devices can be removable and in some embodiments are designed to be disposable. In some embodiments, the contacting portion 108 can be removed from the connector portion 107, with only the contacting portion designed to be disposable. FIG. 7 illustrates one embodiment of the tip 106 of the liquid heat treatment device. As discussed above with respect to the solid-state heat treatment device, the tip 106 can connect to the handle 104 via a threaded connection. The tip may have an O-ring or seal 109 along a proximal end of the connector portion 107 of the tip. The O-ring or seal can help ensure that the liquid used in the heat treatment device does not escape when passing from the handle to the tip. The contacting portion 108 of the tip may have a conformable surface and receives the heated liquid circulating through the device. One advantage of using a conformable surface filled with a liquid is that the tip can mold itself to planar or non-planar treatment surfaces. This can help create a more constant contact pressure than can be easily achieved with rigid tip surfaces. Additionally, the liquid can serve as a thermal reservoir and help ensure temperature uniformity within even very large tips and across the entire treatment surface.

Figure 8:
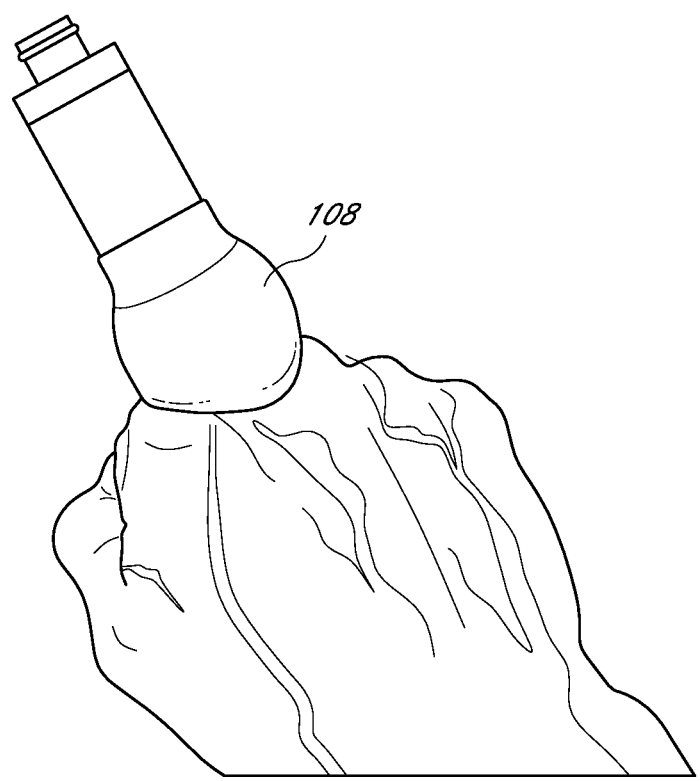
FIG. 8 is a perspective view of the embodiment of FIG. 7 as applied to a curved surface of a patient.

FIG. 8 illustrates the conformity of a liquid tip, which is being used to treat a surface between two knuckles on the hand of a patient. The flexibility of the liquid tip allows it to achieve a contact surface along the entire surface of the area between the two knuckles, whereas otherwise it would be difficult to maintain consistent contact and pressure. A liquid tip can be similarly applied to any treatment surface.

Figure 9:
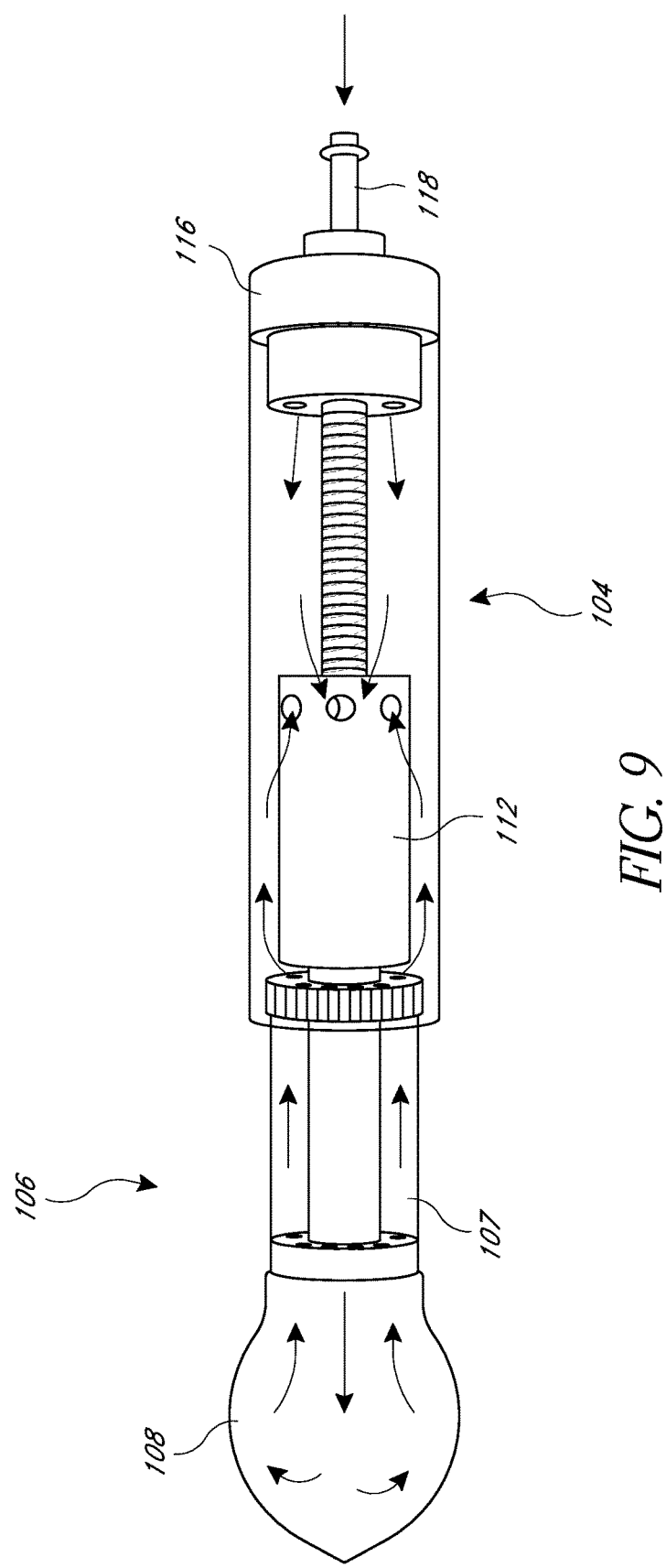
FIG. 9 is a side view of one embodiment of a liquid heat treatment device with flow paths illustrated.

FIGS. 9-13 illustrate in more detail the flow path of the liquid used in the device. This description will refer to the liquid as water, but other liquids can be used. FIG. 9 illustrates a summary of the flow path of the device, with water flowing from the handle 104, through the connector portion 107 and into the contacting portion 108 of the tip, from which the water returns to the handle.

Figure 10:
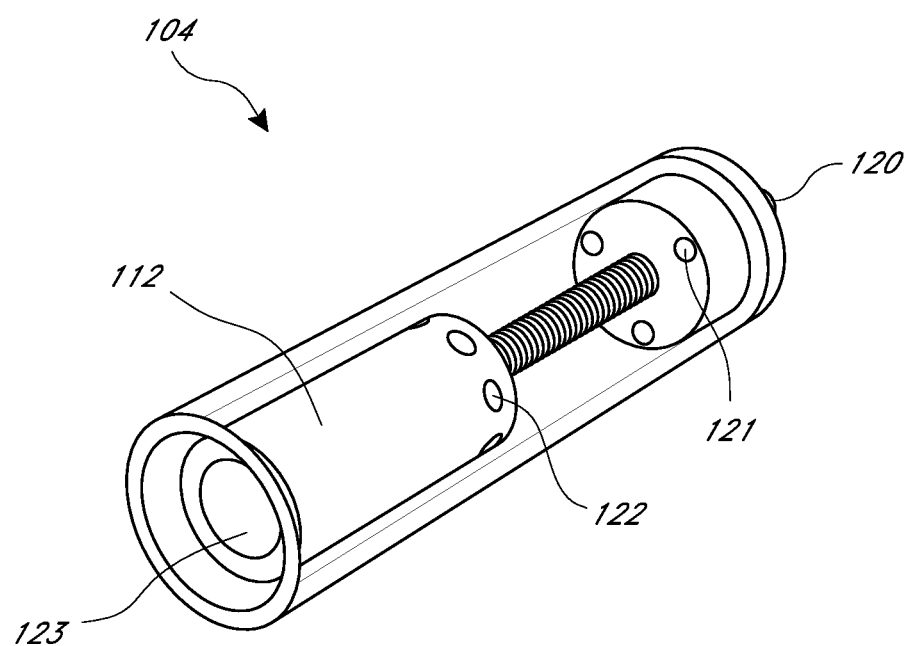
FIG. 10 is a perspective view of one embodiment of the handle of a liquid heat treatment device.

FIG. 10 illustrates the handle 104 of the liquid heat treatment device. Water can enter the handle through the fill tube inlet 120. Once within the handle, the water may circulate throughout the device and it is not necessary to continually supply water through the fill tube inlet. From the fill tube inlet, water enters the handle of the device through the handle inlet 121. The water or fluid then enters the pump housing 112 through the pump inlet ports 122. Water may leave the handle of the device through the pump outlet 123.

Figure 11:
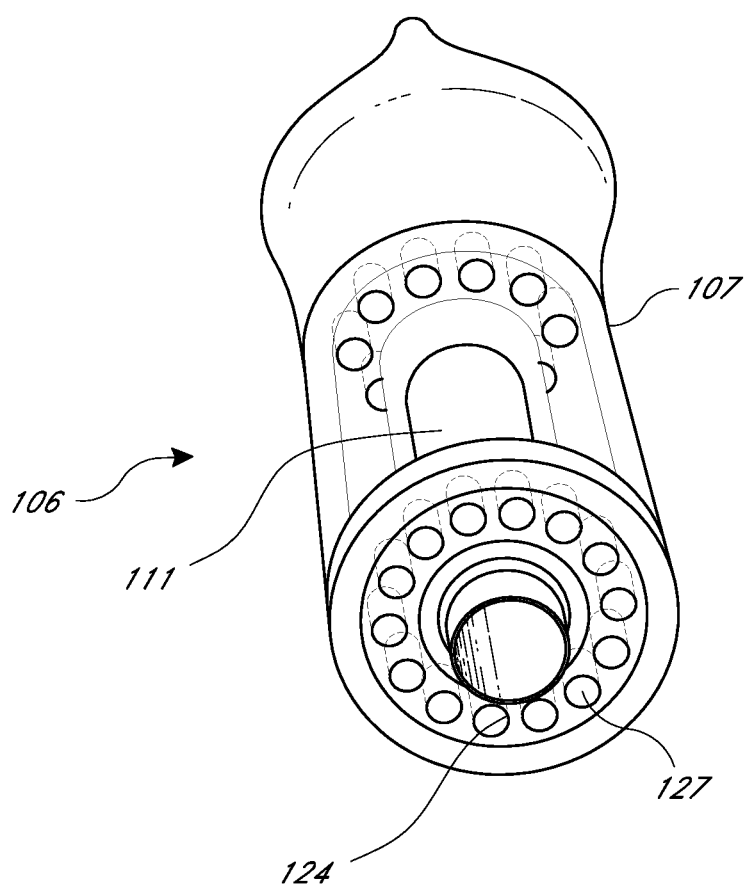
FIG. 11 is a rear perspective view of one embodiment of a replaceable tip of a liquid heat treatment device.
Figure 12:
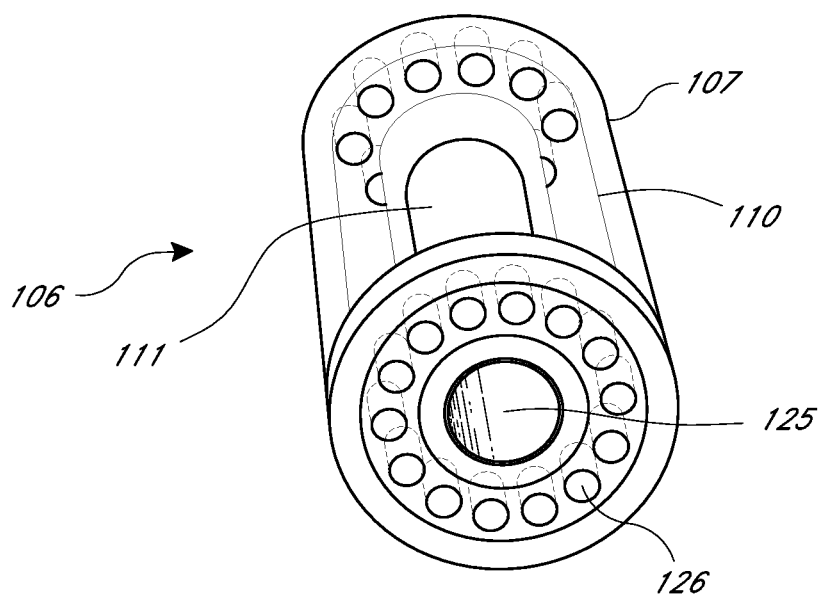
FIG. 12 is a front perspective view of one embodiment of a replaceable tip of a liquid heat treatment device, without a contacting portion.

FIG. 11 illustrates a view of the proximal surface of the connector portion 107 of the tip 106. The connector inlet 124 attaches to the pump outlet 123 such that water exiting the pump may enter the connector inlet. Water passes through the connector inlet and through tube 111 to the contacting portion inlet 125, illustrated in FIG. 12. The contacting portion is not illustrated for ease of viewing the distal surface of the connector portion. Water may flow through and heat the contacting portion, and may then exit the contacting portion through the contacting portion outlets 126. As illustrated, the device can have a plurality of contacting portion outlets, the outlets passing into a chamber 110 located concentrically around the tube 111. From the chamber 110, the liquid passes back into the handle of the device through connector portion outlets 127, as seen in FIG. 11. In some embodiments, each contacting portion outlet 126 may connect through a tube directly to the respective connector portion outlet 127 such that a plurality of tubes connect a plurality of contacting portion outlets to respective connector portion outlets. In other embodiments, the device has only one contacting portion outlet 126 and one connector portion outlet 127. In some embodiments, chamber 110 is not located concentrically around the tube 111 but instead runs parallel to it.

Figure 13:
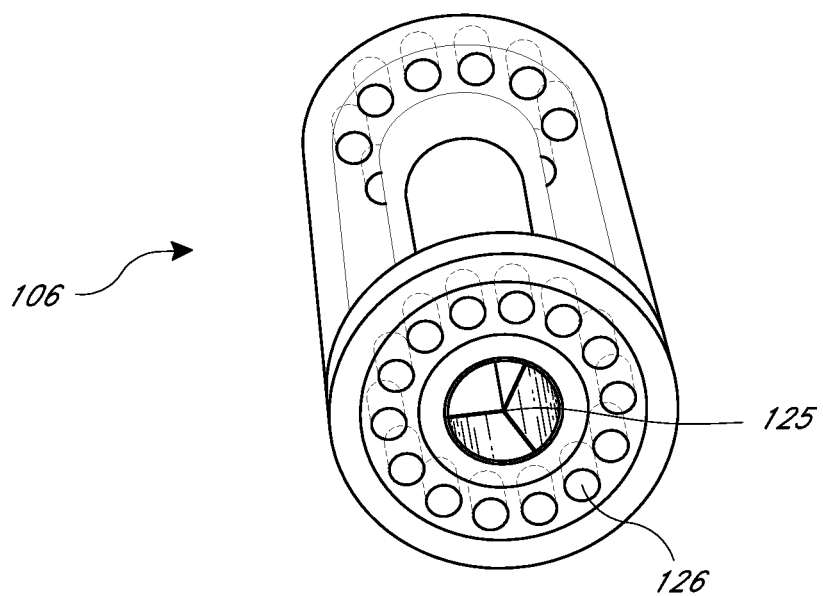
FIG. 13 is a front perspective view of an alternative embodiment of a replaceable tip of a liquid heat treatment device, without a contacting portion.

FIG. 13 illustrates an alternative embodiment of the tube 111 and contacting portion inlet 125 in which the tube 111 splits into a plurality of tubes such that there are multiple contacting portion inlets 125. This may focus or diffuse the stream of liquid, depending on how the inlets are configured. In some embodiments, the tube 111 can extend more distally into the contacting portion to help further focus or diffuse the fluid stream. Such extensions may be made of rigid materials for rigid liquid tips, discussed below, and flexible materials for conformable liquid tips with sufficient rigidity to prevent unwanted deformation but adequate flexibility to permit conformation to a treatment surface if the tip is firmly compressed against a patient.

In some embodiments, it may be advantageous to modify distribution of the fluid stream as it leaves the tube 111 through contacting portion inlet 125 so that it is preferentially directed toward the center or periphery of the contacting portion. One manner of directing the stream toward the periphery could be by rifling the center bore in a process similar to rifling a gun barrel, although with higher lands and deeper grooves required to spin the fluid, imparting a centrifugal force that varies with the water ejection speed. Greater ejection speed imparts more centrifugal force and hence greater radial spread.

When the device is first filled with fluid, it can be beneficial to evacuate any remaining air within the device. In some embodiments, the device can have an egress port that is substantially permeable to air but not to low-pressure water. This can allow air to exit the device but not water. In other embodiments, an egress port can be configured to receive an electric signal that will open it during the filling process but that will close it after the filling process when the device is ready for use. In yet further embodiments, a vacuum pump can be connected to evacuate any air in the hand piece and tip. This can also help serve to verify the integrity of the conformable portion of the tip and whether the tip is securely fastened to the handle.

Figure 14:
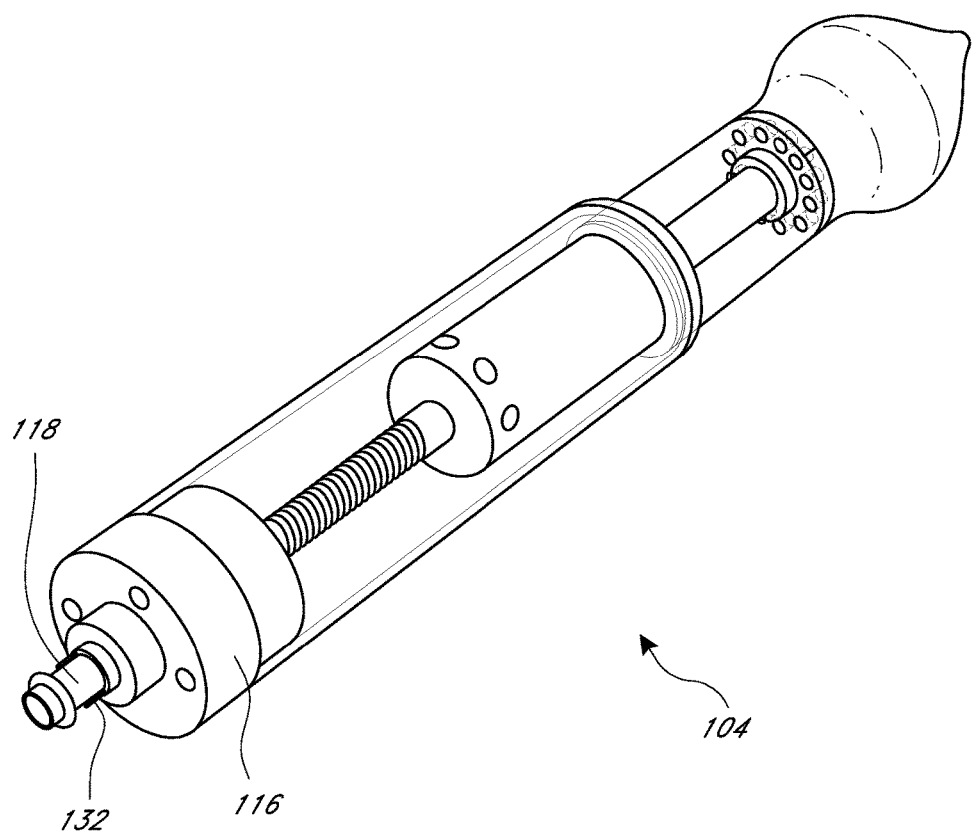
FIG. 14 is a rear perspective view of one embodiment of a liquid heat treatment device.

FIG. 14 provides a view of a proximal end of the liquid heat treatment device. The device can have electrical connectors 132 disposed within an end cap 116. The end cap can have a power source, such as one or more rechargeable batteries, and control circuitry. The connectors 132 can be used to recharge the power source and/or communicate with the control circuitry. The power source can include one or more of the embodiments contemplated above with respect to the solid-state heat treatment device. The control circuitry, in addition to performing the various functions discussed above, can control the functioning of the pump and provide a safety feature by continuously monitoring the voltage of the fluid and immediately cutting off power to the heater or heaters if the fluid voltage is not zero or very close to zero.

In some embodiments, a liquid heat treatment device can maintain a connection to a water source through the fill tube 118. When water returns to the handle from the contacting portion it can circulate out of the device through a portion of the fill tube 118 or through a separate outlet tube, rather than returning through the pump to the contacting portion of the device. In some embodiments, the water can be heated in a base station, described below, or obtained from a hot water supply line, and does not need to be heated within the device. In some embodiments, the treatment device can connect to a hot water supply line and a cold water supply line, and the device can have a mixing valve that can be configured to adjust the relative hot and cold water proportions to achieve a desired treatment temperature at the tip. The closer the mixing valve is positioned to the tip, the quicker and more precisely it is able to respond to and correct temperature fluctuations.

Figure 15:
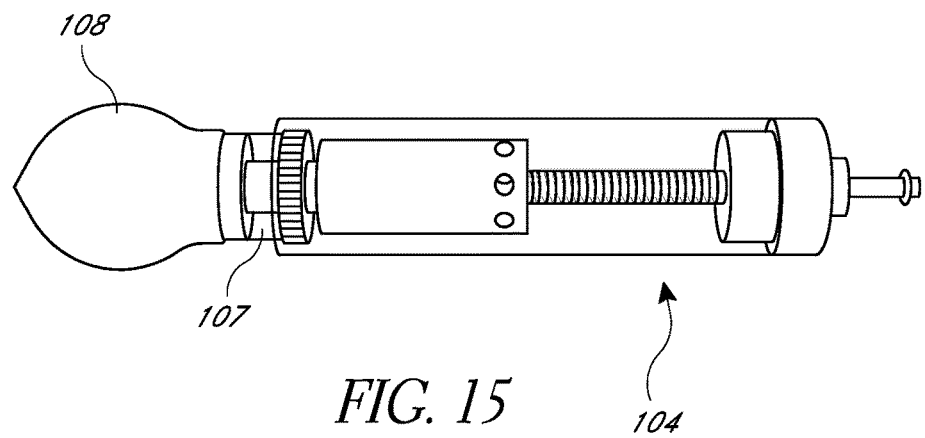
FIG. 15 is a side view of an alternative embodiment of a liquid heat treatment device.

The liquid heat treatment device contemplates various embodiments of the tip 106. FIG. 15 illustrates one embodiment of the liquid heat treatment device in which the connector portion 107 of the tip is significantly shorter than the embodiments previously illustrated and discussed. The connector portion 107 can be long enough for convenient handling. As discussed with regard to the solid-state heat treatment device, in different embodiments the contacting portion 108 can be of various sizes.

Figure 16:
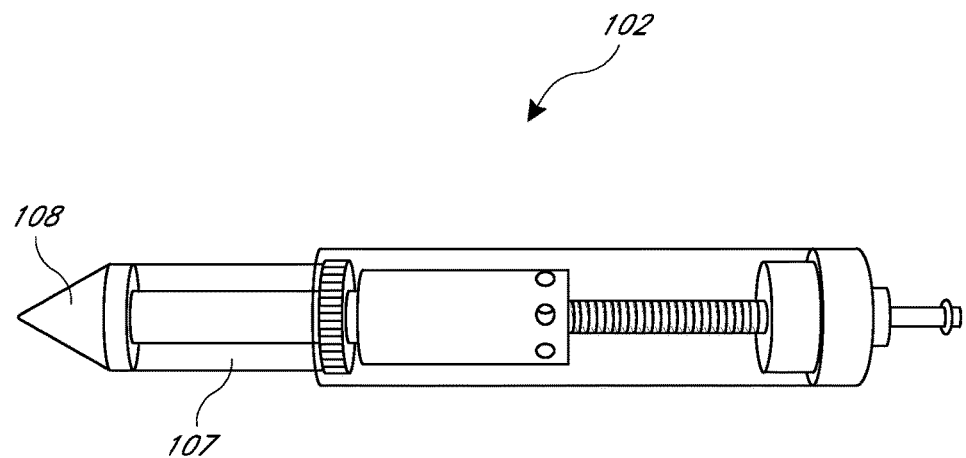
FIG. 16 is a side view of an embodiment of a liquid heat treatment device with a rigid tip.

In further embodiments, such as the embodiment of FIG. 16, the contacting portion 108 of the tip can have a rigid surface rather than the conformable surface discussed above. The rigid tip can be molded using a thermally conductive plastic, or in other embodiments can be formed from metal. The rigid tip, whether composed of plastic or metal, can have very thin walls that enhance heat conductivity from the water into the patient's skin, mucous membrane, or other tissue at the site of treatment. Graphene may prove to be a particularly beneficial material for use when constructing the rigid tip because it has a high thermal conductivity and is very rigid, but also has exceptional strength that would permit it to be very thin around the tip. Rigid tips can be used for precise treatment of small areas.

In some embodiments, a rigid tip can have a narrow, elongated loop that connects a single contacting portion inlet to a single contacting portion outlet. The loop can be formed of a thermally conductive material, such as copper or aluminum, and can include a tube bent sharply at a distal end of the contacting portion. The apex of the bend can serve as the patient contact area. In some embodiments, the loop can have a covering over it that may contact the patient. In other embodiments, the loop itself can contact the patient.

Figure 17:
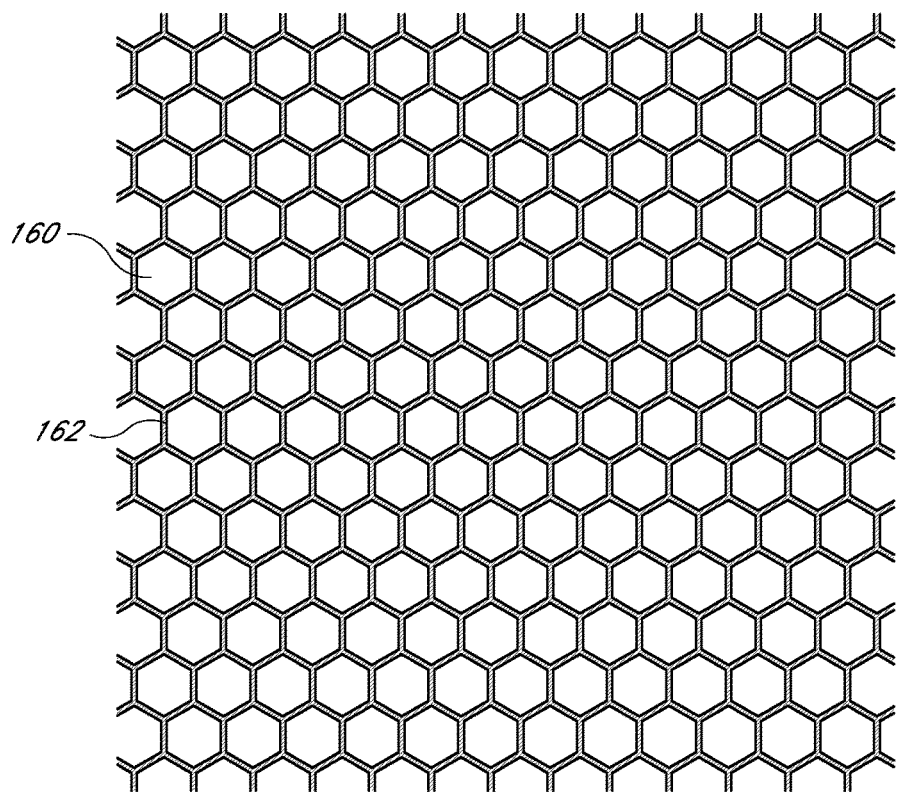
FIG. 17 is a view of one embodiment of a material used with a tip of a heat treatment device.
Figure 18:
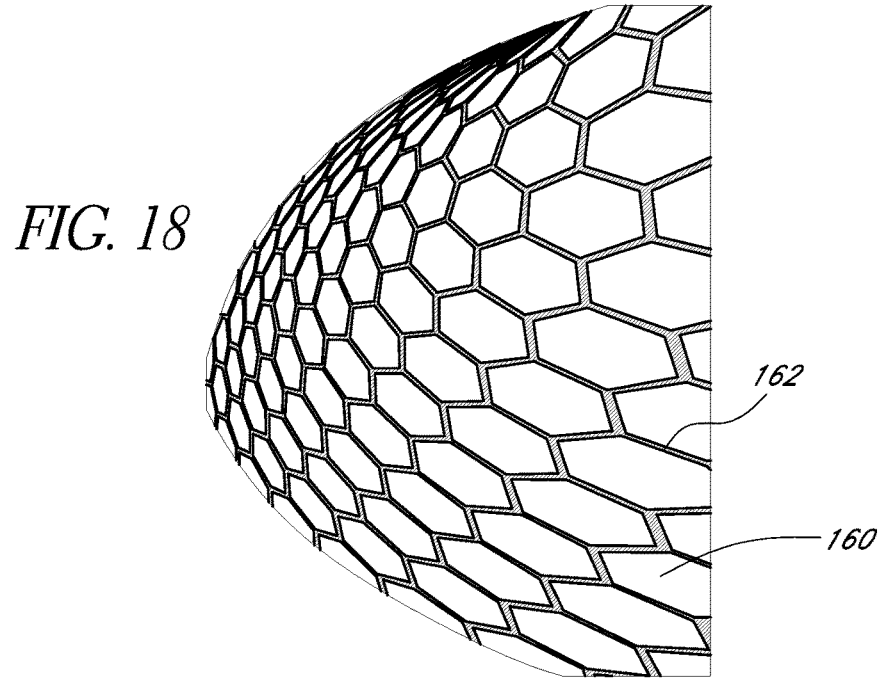
FIG. 18 is a perspective view of the embodiment of FIG. 17 when flexed.

In some embodiments, certain materials and structures can be beneficial for constructing the contacting portion 108 of the liquid heat treatment device. FIGS. 17-21 illustrate one embodiment of a material that can be used with conformable liquid tips. FIG. 17 illustrates a top view of the material, which can have a plurality of metal or graphene hexagons 160 bonded to a thermally conductive sheet 162. In some embodiments, the metal or graphene can be formed into geometrical configurations other than hexagons. FIG. 18 illustrates how the material can flex to form three-dimensional structures without wrinkling. This can prove beneficial when used with a conformable tip, as discussed above, such that the contacting portion can maintain contact across the entire area of treatment.

Figure 19:
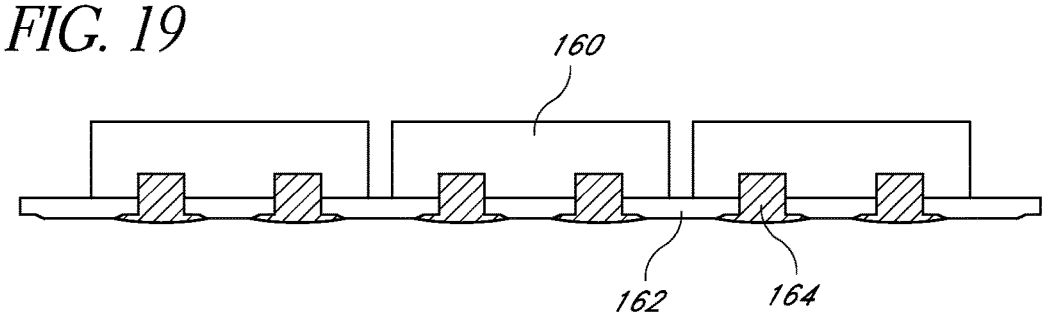
FIG. 19 is a side view of one embodiment of a material used with a tip of a heat treatment device.
Figure 20:
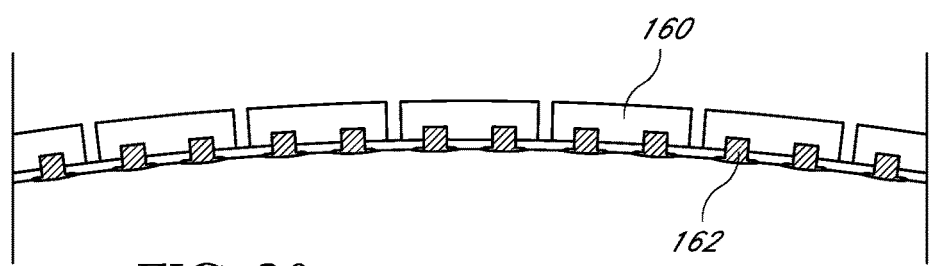
FIG. 20 is a side view of the embodiment of FIG. 19 as flexed onto a concave surface.
Figure 21:
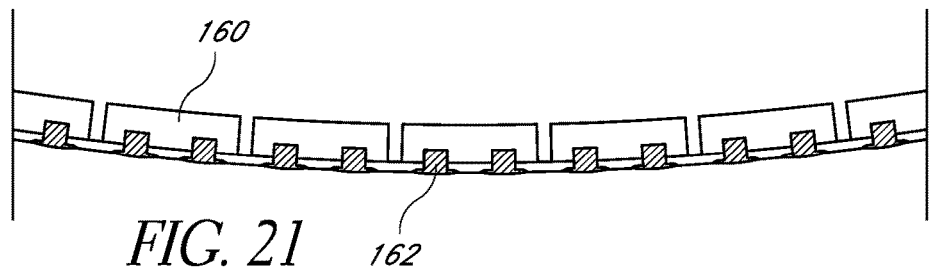
FIG. 21 is a side view of the embodiment of FIG. 19 as flexed onto a convex surface.

FIG. 19 illustrates a side view of one embodiment of a material used to construct the conformable surface of a tip. Rivets 164 can be used to attach metallic hexagons or other geometric segments 160 to the rubber sheet 162 to lock them into place so that they cannot rotate. The rivets can also serve to seal the sheet by compressing it so that water cannot exit and so that patient fluids cannot enter through the sheet, and also to present a larger surface area to the water so that heat from it more readily conducts into the outer hex segments. FIGS. 20 and 21 illustrate the ease and ability of this type of structure to flex into a concave surface (FIG. 20) and into a convex surface (FIG. 21).

Because treatment temperatures can be above what many patients would consider comfortable, or may even find painful, it can be beneficial to limit or minimize the patient's discomfort or pain. One way to limit discomfort is to apply principles of sensory nerve adaption: the speed at which temperature applied to the body changes will significantly influence the nature of a perceived stimulus, potentially rendering an otherwise noxious stimulus acceptable. One way to take advantage of this concept is to apply the contacting portion of the device against the tissue desired to be treated before the contacting portion reaches a desired treatment temperature. This will be referred to as treatment "with adaptation." As an example, if the desired treatment temperature is 130 degrees Fahrenheit, treatment with adaptation can include placing the contacting portion of the device against the tissue when the contacting portion is at room temperature or has been heated slightly, and then heating the contacting portion to 130 degrees.

Figure 22:
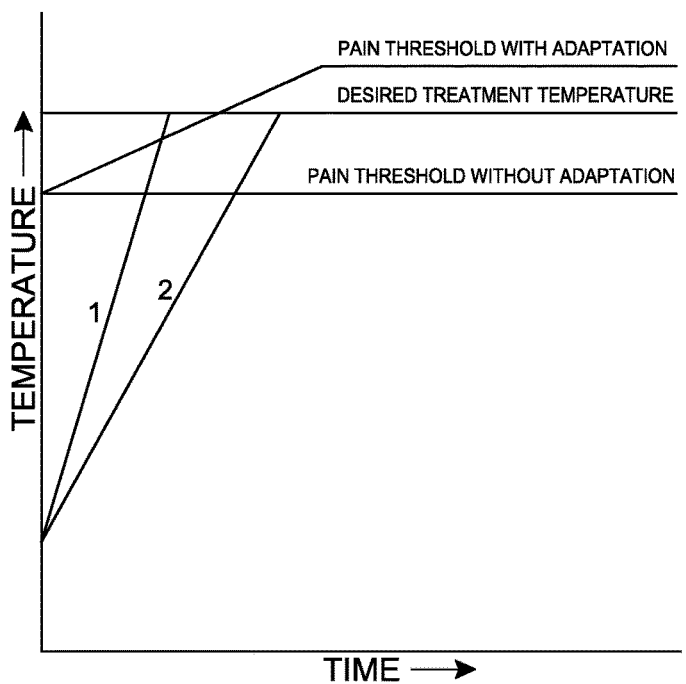
FIG. 22 is a graph of two embodiments of a treatment procedure, plotted as applied temperature over time, on which a desired treatment temperature, a pain threshold without adaptation, and a pain threshold with adaptation are displayed.

FIG. 22 illustrates this concept. FIG. 22 charts the temperature of the contacting portion of the device against time of application. It illustrates two separate treatment procedures—a first treatment procedure labeled "1," and a second treatment procedure labeled "2." FIG. 22 also has a marked pain threshold without adaptation at a particular temperature, a desired treatment temperature above the pain threshold temperature without adaptation, and a plot of the pain threshold temperature with adaptation. The pain threshold with adaptation at time zero is equal to the pain threshold without adaptation, but increases as time increases to a maximum pain threshold temperature with adaptation. This chart is but an example; in practice the pain threshold temperature without adaptation, the desired treatment temperature, and the pain threshold temperature with adaptation could be positioned at significantly different locations on the graph. The only necessary relationship between the three is that the pain threshold temperature with adaptation reach a temperature greater than the pain threshold temperature without adaptation.

Whether a particular patient will experience pain when the contacting portion at a particular temperature is placed in contact with the patient depends on whether that temperature is above or below the particular pain threshold without adaptation of that patient. For both of the illustrated treatment procedures, the contacting portion of the device was placed in contact with the patient at an initial temperature below the desired treatment temperature and below the pain threshold temperature without adaptation. As illustrated, both the first and second treatment procedures eventually reach the desired treatment temperature. However, the first treatment procedure increases in temperature more quickly than the second treatment procedure. In doing so, the first treatment procedure reaches a temperature above the pain threshold temperature with adaptation, and the patient experiences pain. The second treatment procedure, however, increases temperature slowly enough such that it reaches the desired treatment temperature without crossing the pain threshold temperature with adaptation, and the patient experiences no unnecessary discomfort.

In some embodiments, treatment procedures with adaptation take at least 2 seconds from when the tip is first positioned against a treatment area to when the tip reaches the desired treatment temperature. In some embodiments, treatment with adaptation can take at least 5 seconds for the tip to reach the desired treatment temperature. In further embodiments, treatment with adaptation can take at least 10, 15, 20, or 30 seconds for the tip to reach the desired treatment temperature.

In FIG. 22, the desired treatment temperature is below the maximum pain threshold temperature with adaptation. Where the desired treatment temperature is above the maximum pain threshold temperature with adaptation, it is impossible to treat the patient without providing some amount of pain or discomfort. While the tip heats to the desired treatment temperature, however, it is possible to minimize the time at which the temperature of the contacting portion of the tip is above the pain threshold temperature.

Figure 23:
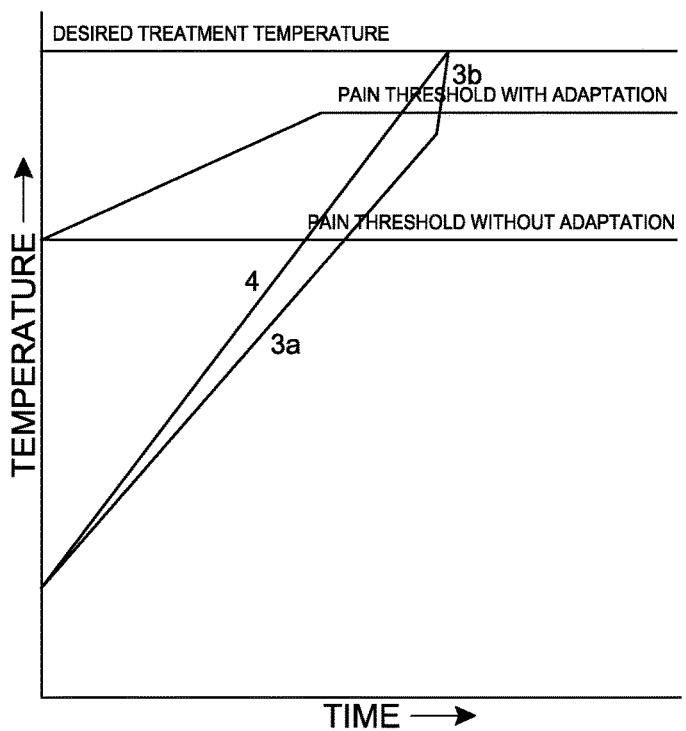
FIG. 23 is a graph of two alternative embodiments of a treatment procedure, plotted as applied temperature over time, on which a desired treatment temperature, a pain threshold without adaptation, and a pain threshold with adaptation are displayed.

This approach, illustrated in FIG. 23, is achieved by applying an initially slower rate of temperature change, keeping the temperature under the pain threshold, and then quickly increasing the rate of temperature change to rapidly reach the desired treatment temperature. The two treatment procedures illustrated in FIG. 23—treatment procedure 4, marked by line "4," and treatment procedure 3, marked by lines "3a" and "3b"—illustrate two different methods of reaching a desired treatment temperature from the same initial temperature in the same amount of time, but which provide differing amounts of time above the patient's pain threshold. In treatment procedure 4, the temperature is increased at a constant rate to the desired treatment temperature. In treatment procedure 3, in contrast, the temperature is increased at a lower rate of heating in a first phase, as illustrated by line "3a," and then quickly increased to the desired treatment temperature in a second phase, as illustrated by line "3b." As can be seen in the Figure, treatment procedure 4 spends more time above the pain threshold than treatment procedure 3.

The heating profiles of FIGS. 22 and 23, and the discussed embodiments of heat treatment with adaptation generally, can be used in both the solid-state and liquid heat treatment device. In some embodiments of a liquid heat treatment device, the biphasic approach illustrated by treatment procedure 3 in FIG. 23 can be achieved by having a heater or multiple heaters that quickly heat the fluid circulating within the liquid heat treatment device. Depending on the particular fluid used, the amount of fluid used, and the size of the device and contacting portion, rapidly changing the temperature of the fluid can require a significant amount of energy.

Figure 24:
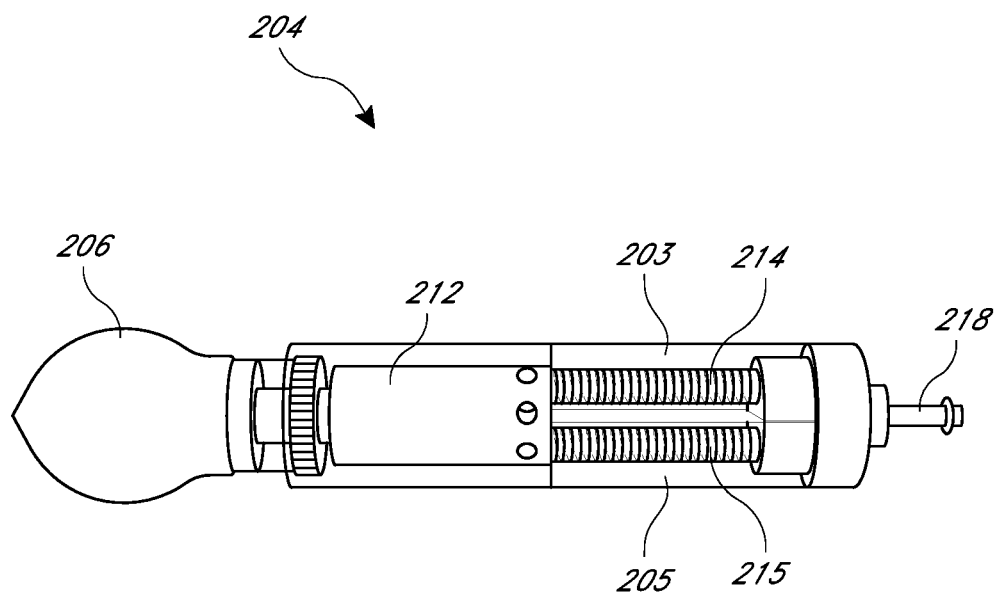
FIG. 24 is a side view of an alternative embodiment of a liquid heat treatment device.

FIG. 24 illustrates an embodiment of the liquid heat treatment device that can implement the biphasic approach more quickly than heating the same water to a higher temperature in the second phase of the treatment. In FIG. 24, the handle 204 of the device has two separate chambers—a first chamber 203 and a second chamber 205. Each chamber can have a heater; the first chamber can have a first heater 214 and the second chamber can have a second heater 215. Each chamber can further have its own temperature sensor (not shown), its own input from the fill tube 218, and its own output to the section of the handle that has the pump housing 212. In some embodiments, each chamber can have its own pump and its own output to the tip 206.

In some embodiments, the first chamber can be configured to heat fluid to a first temperature, and the second chamber can be configured to heat fluid to a second temperature. In some embodiments, both the first temperature and the second temperature are greater than the desired treatment temperature; in other embodiments, the first temperature is lower than the desired treatment temperature and the second temperature is greater than the first temperature. In some embodiments, water from the first chamber is heated to a first temperature from a heater (not shown) located within the pump housing 212.

During the first phase of the biphasic approach, the first chamber can be open and in fluid communication with the section of the handle that has the pump housing 212. Liquid that reaches the tip 206 will approach a temperature substantially equal to the first temperature. In the second phase of the biphasic approach, the second chamber can open, creating a connection between the second chamber and the portion of the handle that has the pump housing 212, thereby allowing fluid from the second chamber to enter circulation. Liquid that reaches the tip 206 will approach a temperature substantially equal to the second temperature. In some embodiments, the second temperature can be calibrated such that the combination of water from the second chamber with water already circulating through the device will be at a desired temperature. In some embodiments, the first chamber can close prior to opening the second chamber.

In some embodiments, the first and second chambers can be opened and/or closed manually. In other embodiments, the control circuitry can be configured to automatically close or open either of the chambers based on a predetermined trigger. In some embodiments, the second chamber can be configured to open after a set amount of time. In other embodiments, the second chamber can be configured to open once the fluid in the tip of the device reaches a set temperature.

The first and second chambers can be thermally insulated with respect to each other to help keep the water in each chamber at its desired temperature. Peripheral thermal insulation around the external surface of the handle can be used in both the dual-chamber embodiment of FIG. 24 and the single-chamber embodiments discussed previously, in order to minimize heat loss, limit energy requirements, and limit the external temperature of the handle. Insulation is not displayed in these figures for ease of viewing, and is not necessary in all embodiments.

Figure 25:
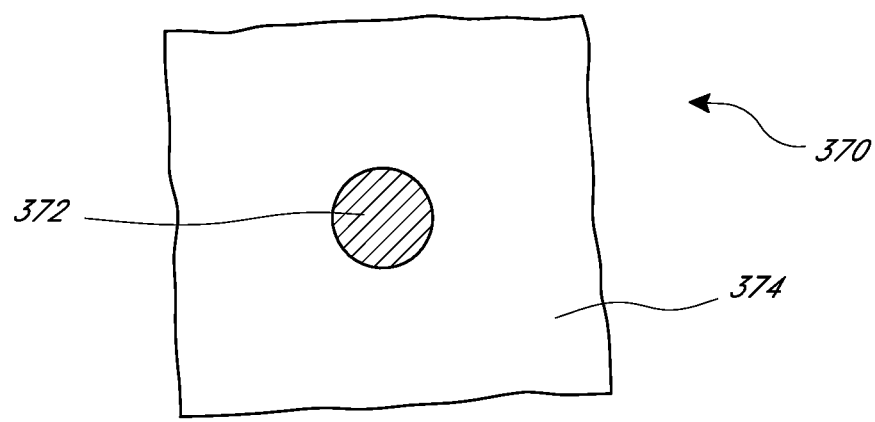
FIG. 25 is a top view of one embodiment of an application barrier.
Figure 26:
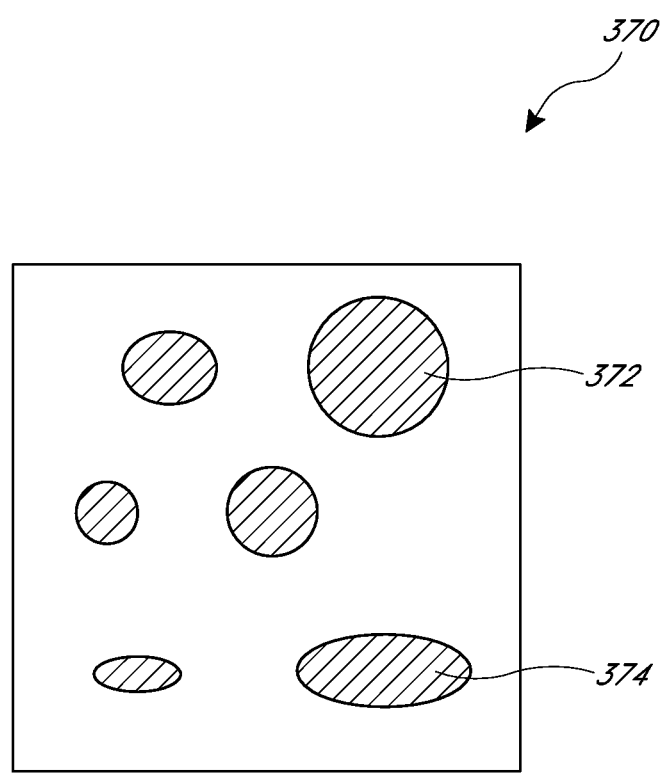
FIG. 26 is a top view of an alternative embodiment of an application barrier.

In some embodiments, as discussed above, the tip is designed to be sufficiently inexpensive that it can be discarded after a single use. However, in order to minimize the need for cleaning higher-cost tips that a user does not desire to throw away, in some embodiments a barrier can be used between the patient and the application tip to preserve sterility and prevent infection. The barrier can be formed of a variety of materials, such as polyethylene, thin copper or aluminum foil, or other plastics, metals, or thermally conductive materials. The barrier can be a small size, sized to fit over the treatment area, or it can be larger for easier handling. As illustrated in FIG. 25, the barrier 370 can have a plastic portion 374 and a small island 372 composed of a foil. The plastic portion can be clear to help in localizing the treatment area and placing the foil 372 on top of the specific treatment area. In use, the contacting portion of the treatment device is placed against the island 372, and heat is transferred through to the treatment area. In other embodiments, such as that illustrated in FIG. 26, the application barrier 370 can have a plurality of islands 372, each of a different size or shape for treatment of different sized and shaped infections or injuries. In other embodiments, the sheet 374 can function as a thermal insulator to ensure that heat is transferred primarily to the lesion or site of infection and not to the area around it, particularly when the contacting portion of the tip is larger than the lesion or area of treatment. This can be achieved by forming the sheet 374 of insulating materials, and/or making the sheet thicker or including pockets of air between different layers of the sheet 374.

Figure 27:
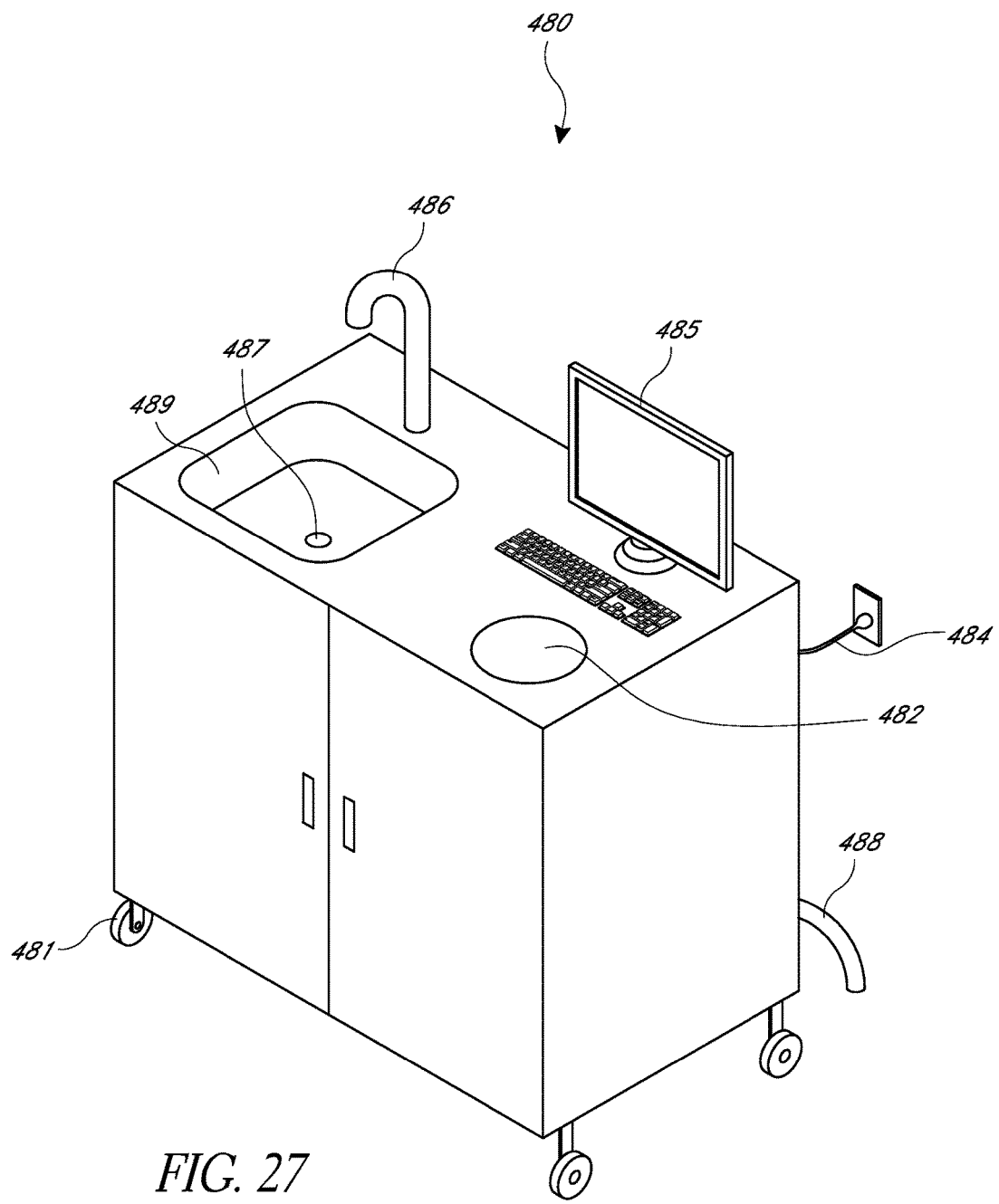
FIG. 27 is a perspective view of a base station that can be used with a heat treatment device.

In some embodiments, the treatment device can be associated with a base station. FIG. 27 illustrates one embodiment of a base station. The base station 480 can be located in a permanent or semi-permanent location, and in some embodiments can have wheels 481. The base station can have a source of power 482 for the heat treatment device which, in some embodiments, can be an inductive charging device, as illustrated; in other embodiments it can have a physical connection to the source of power. The base station can be plugged into an outlet through a power line 484 or can receive power through its own portable power source. The base station can also have a source of water 486 that can be used to refill embodiments of the heat treatment device that rely on fluid to transfer heat throughout the device. The water source 486 can run to a standard faucet or a hose, tubing, and/or valve configured to attach to the fill tube of the device. In some embodiments, the base station can have multiple sources of water, one connected to a hot water supply and one connected to a cold water supply. The base station can also have a drain 487, and both the drain 487 and water source 486 can be associated with a receptacle 489 and connected to one or more water lines 488.

In some embodiments, the water source can be within the receptacle and the receptacle can be sized to couple with the proximal end of a heat treatment device. The water source can connect to a valve or other element that can mate with the fill tube and inject water into the device. In some embodiments, the fill tube can be a male connector and the valve or other element can have a female connector. In other embodiments, the fill tube can have a female connector and the valve or other device can have a male connector. In some embodiments, the receptacle can have both a drain and a water source within it, and inserting the device within the receptacle can allow for filling the device and/or draining the device. In some embodiments, the receptacle can also have a physical power connection for the heat treatment device. In some embodiments, the heat treatment device can charge through inductive charging while it is within the receptacle.

The base station can also have cabinets or other storage devices that can store a variety of treatment tips to be used with the heat treatment device. In some embodiments, the base station can have a network connection and can be integrated into the IT system of a hospital or clinic, allowing the base station to send alerts if it is low in replaceable tips, application barriers, or other components used with heat treatment devices. In some embodiments, the base station can have a computer 483 that can be used to program a heat treatment device, download treatment data, set temperatures and thresholds, and otherwise interact with the heat treatment device.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A heat treatment device for therapeutically treating an affected area of a patient using heat, the heat treatment device comprising:
   a body comprising a handle portion, a rigid tip portion coupled to the handle portion, and a fluid channel extending through the handle portion to the rigid tip portion such that the handle portion is in fluid communication with the rigid tip portion, wherein the rigid tip portion being configured to be removable and replaceable with one of a plurality of rigid tip portions of different shapes and sizes;
   a power source supported by the body, wherein an interior of the fluid channel being at least partially rifled and being configured to impart a preferential radial spread to a fluid disposed within the fluid channel;
   at least one heating element disposed in the handle portion, the at least one heating element being in electrical communication with the power source such that the at least one heating element is configured to heat a fluid disposed within the fluid channel;
   a pump supported by the handle portion, the pump being configured to urge fluid through the fluid channel from the handle portion into the rigid tip portion of the heat treatment device; and
   a control circuitry supported by the body of the heat treatment device, the control circuitry being configured to:
      automatically recognize a particular rigid tip portion having a particular size and a particular shape through an electronic identifier, wherein the electronic identifier is placed in the rigid tip portion and recognizable by the control circuitry; and
      adjust a current flowing to the at least one heating element when the heat treatment device is in use, wherein the at least one heating element is configured to heat a fluid disposed in the fluid channel of the handle portion and the pump is configured to facilitate transfer of the fluid into the recognized particular rigid tip portion of the heat treatment device to heat the recognized particular rigid tip portion to a desired temperature.

2. The heat treatment device of claim 1, further comprising a return fluid channel extending from the rigid tip portion toward the handle portion and in fluid communication with the fluid channel, the fluid channel and the return fluid channel forming a circulatory pathway to allow fluid to be circulated within the heat treatment device.

3. The heat treatment device of claim 1, wherein said at least one heating element comprises a first heating element and a second heating element, and wherein the handle portion comprises a first chamber with a said first heating element and a second chamber with said second heating element, the first chamber configured to heat the fluid in the first chamber to a first temperature below the desired temperature, and the second chamber configured to heat the fluid in the second chamber to a second temperature greater than the first temperature.

4. The heat treatment device of claim 3, wherein the first chamber and the second chamber are in fluid communication with the fluid channel.

5. The heat treatment device of claim 1, wherein the rigid tip portion further comprises a temperature sensor in electrical communication with the control circuitry for maintaining the rigid tip portion at the desired temperature.

6. The heat treatment device of claim 1, wherein the heat treatment device is modular such that the rigid tip portion is separable and removable from the body to allow a replacement rigid tip portion to be mounted onto the body after the rigid tip portion is removed.

7. The heat treatment device of claim 6, wherein the body comprises a connector portion configured to be coupled with a respective connector portion of the rigid tip portion.

8. The hat treatment device of claim 6, wherein the replacement rigid tip portion comprises an electronic identifier that is recognizable by the control circuitry, the control circuitry being configured to adjust the current flowing to at least one heating element of the replacement rigid tip portion when the device is in use in response to the electronic identifier of the replacement rigid tip portion.

9. The heat treatment device of claim 1, wherein the preferential radial spread imparted to the fluid disposed within the fluid channel may be controlled by the pump.

10. The heat treatment device of claim 1, further comprising a pressure sensor configured to measure a force applied by the rigid tip portion against the affected area and to provide a feedback signal to a physician that is indicative of the force measured by the pressure sensor.

11. The heat treatment device of claim 1, wherein the at least one heating element is disposed within the rigid tip portion.

12. The heat treatment device of claim 1, wherein the at least one heating element is a resistive heating element.

13. The heat treatment device of claim 1, wherein the control circuitry is configured to measure a temperature of the rigid tip portion of the heat treatment device by sampling a resistance of the resistive heating element.

14. The heat treatment device of claim 1, wherein the rigid tip portion comprises a tip housing, and wherein the at least one heating element is disposed at least partially within the tip housing and extending from a distal end of the rigid tip.

* * * * *